(12) United States Patent
Grychowski et al.

(10) Patent No.: US 7,270,123 B2
(45) Date of Patent: Sep. 18, 2007

(54) NEBULIZER APPARATUS AND METHOD

(75) Inventors: Jerry Grychowski, Lake Zurich, IL (US); Martin P. Foley, London (CA); Michael Nuttall, London (CA)

(73) Assignee: Trudell Medical International, Ontario (CA)

( * ) Notice: Subject to any disclaimer, the term of this patent is extended or adjusted under 35 U.S.C. 154(b) by 321 days.

(21) Appl. No.: 10/918,656

(22) Filed: Aug. 12, 2004

(65) Prior Publication Data

US 2005/0081844 A1   Apr. 21, 2005

Related U.S. Application Data

(60) Provisional application No. 60/494,892, filed on Aug. 13, 2003.

(51) Int. Cl.
*A61M 11/00* (2006.01)

(52) U.S. Cl. ............... 128/200.14; 128/200.18; 128/200.21

(58) Field of Classification Search ........... 128/200.14, 128/200.16–200.18, 200.21, 200.25, 203.12, 128/203.14–203.17, 203.26, 203.27, 204.14, 128/204.27, 205.24
See application file for complete search history.

(56) References Cited

U.S. PATENT DOCUMENTS

| | | | |
|---|---|---|---|
| 2,535,844 A | 12/1950 | Emerson | |
| 2,882,026 A | 4/1959 | Eichelman | |
| 3,269,665 A | 8/1966 | Cheney | |
| 3,467,092 A | 9/1969 | Bird et al. | |
| 3,490,697 A * | 1/1970 | Best, Jr. ............. | 239/102.2 |
| 3,580,249 A | 5/1971 | Takaoka | |
| 3,584,621 A | 6/1971 | Bird et al. | |
| 3,630,196 A | 12/1971 | Bird et al. | |
| 3,658,059 A | 4/1972 | Steil | |
| 3,664,337 A | 5/1972 | Lindsey et al. | |
| 3,826,255 A | 7/1974 | Havstad et al. | |
| 3,838,686 A | 10/1974 | Szekely | |
| 3,874,379 A | 4/1975 | Enfield et al. | |
| 3,990,442 A | 11/1976 | Patneau | |
| 4,093,124 A | 6/1978 | Morane et al. | |
| 4,094,317 A | 6/1978 | Wasnich | |
| 4,106,503 A | 8/1978 | Rosenthal et al. | |
| 4,116,387 A | 9/1978 | Kremer, Jr. et al. | |

(Continued)

FOREIGN PATENT DOCUMENTS

DE    199 02 847 C1    5/2000

(Continued)

OTHER PUBLICATIONS

Photographs of nebulizer manufactured by PARI GmbH with detachable gas flow interrupter believed to have been publicly available prior to Feb. 13, 1996.

*Primary Examiner*—Justine R. Yu
*Assistant Examiner*—Adam Brandt
(74) *Attorney, Agent, or Firm*—Brinks Hofer Gilson & Lione

(57) ABSTRACT

A nebulizer for efficiently and reliably delivering aerosolized fluid to an inhaling patient is disclosed. The nebulizer, in one embodiment, includes a fluid channel air inlet and fluid channel air inlet valve responsive to either a manual force external of the nebulizer, or a patient's breathing, to begin the nebulization process. The nebulizer also includes a fluid return channel to a fluid source, such as a removable vial, containing fluid to be aerosolized.

12 Claims, 19 Drawing Sheets

U.S. PATENT DOCUMENTS

| | | | |
|---|---|---|---|
| 4,150,071 A * | 4/1979 | Pecina | 261/78.2 |
| 4,198,969 A | 4/1980 | Virag | |
| 4,251,033 A | 2/1981 | Rich et al. | |
| 4,268,460 A | 5/1981 | Boiarski et al. | |
| 4,333,450 A | 6/1982 | Lester | |
| 4,413,784 A | 11/1983 | Dea | |
| 4,470,412 A | 9/1984 | Nowacki et al. | |
| 4,588,129 A | 5/1986 | Shanks | |
| 4,620,670 A | 11/1986 | Hughes | |
| 4,657,007 A | 4/1987 | Carlin et al. | |
| 4,674,491 A | 6/1987 | Brugger et al. | |
| 4,677,975 A | 7/1987 | Edgar et al. | |
| 4,746,067 A | 5/1988 | Svoboda | |
| 4,758,224 A | 7/1988 | Siposs | |
| 4,792,097 A | 12/1988 | Kremer, Jr. et al. | |
| 4,809,692 A | 3/1989 | Nowacki et al. | |
| 4,832,015 A | 5/1989 | Nowacki et al. | |
| 4,984,158 A | 1/1991 | Hillsman | |
| 5,020,530 A | 6/1991 | Miller | |
| 5,054,477 A | 10/1991 | Terada et al. | |
| 5,054,478 A | 10/1991 | Grychowski et al. | |
| 5,086,765 A | 2/1992 | Levine | |
| 5,165,392 A | 11/1992 | Small | |
| 5,167,506 A | 12/1992 | Kilis et al. | |
| 5,170,782 A | 12/1992 | Kocinski | |
| 5,241,954 A | 9/1993 | Glenn | |
| 5,277,175 A | 1/1994 | Riggs et al. | |
| 5,280,784 A | 1/1994 | Kohler | |
| 5,299,565 A | 4/1994 | Brown | |
| 5,301,662 A | 4/1994 | Bagwell et al. | |
| 5,301,663 A | 4/1994 | Small, Jr. | |
| 5,309,900 A | 5/1994 | Knoch et al. | |
| 5,312,046 A | 5/1994 | Knoch et al. | |
| 5,318,015 A | 6/1994 | Mansson et al. | |
| 5,363,842 A | 11/1994 | Mishelevich et al. | |
| 5,398,714 A | 3/1995 | Price | |
| 5,458,136 A | 10/1995 | Jaser et al. | |
| 5,479,920 A | 1/1996 | Piper et al. | |
| 5,487,378 A | 1/1996 | Robertson et al. | |
| 5,505,192 A | 4/1996 | Samiotes et al. | |
| 5,505,193 A | 4/1996 | Ballini et al. | |
| 5,511,538 A | 4/1996 | Haber et al. | |
| 5,515,842 A | 5/1996 | Ramseyer et al. | |
| 5,520,166 A | 5/1996 | Ritson et al. | |
| 5,533,497 A * | 7/1996 | Ryder | 128/200.21 |
| 5,533,501 A | 7/1996 | Denyer | |
| 5,549,102 A | 8/1996 | Lintl et al. | |
| 5,570,682 A | 11/1996 | Johnson | |
| 5,584,285 A | 12/1996 | Salter et al. | |
| 5,613,489 A | 3/1997 | Miller et al. | |
| 5,617,844 A | 4/1997 | King | |
| 5,622,162 A | 4/1997 | Johansson et al. | |
| 5,630,409 A | 5/1997 | Bono et al. | |
| 5,687,912 A | 11/1997 | Denyer | |
| 5,792,057 A | 8/1998 | Rubsamen et al. | |
| 5,803,078 A | 9/1998 | Brauner | |
| 5,823,179 A | 10/1998 | Grychowski et al. | |
| 5,875,774 A | 3/1999 | Clementi et al. | |
| 6,044,841 A | 4/2000 | Verdun et al. | |
| 6,116,233 A | 9/2000 | Denyer et al. | |
| 6,129,080 A | 10/2000 | Pitcher et al. | |
| 6,131,568 A | 10/2000 | Denyer et al. | |
| 6,223,745 B1 | 5/2001 | Hammarlund et al. | |
| 6,237,589 B1 | 5/2001 | Denyer et al. | |
| 6,450,163 B1 * | 9/2002 | Blacker et al. | 128/200.18 |
| 6,543,448 B1 * | 4/2003 | Smith et al. | 128/203.15 |
| 6,595,203 B1 * | 7/2003 | Bird | 128/200.21 |
| 6,612,303 B1 | 9/2003 | Grychowski et al. | |
| 6,644,304 B2 | 11/2003 | Grychowski et al. | |
| 6,929,003 B2 * | 8/2005 | Blacker et al. | 128/203.12 |
| 7,051,731 B1 * | 5/2006 | Rogerson | 128/200.23 |
| 2001/0032643 A1 * | 10/2001 | Hochrainer et al. | 128/200.21 |
| 2002/0020762 A1 | 2/2002 | Selzer et al. | |
| 2002/0157663 A1 | 10/2002 | Blacker et al. | |
| 2003/0005929 A1 | 1/2003 | Grychowski et al. | |
| 2003/0015193 A1 | 1/2003 | Grychowski et al. | |
| 2003/0136399 A1 * | 7/2003 | Foley et al. | 128/200.14 |
| 2004/0031485 A1 * | 2/2004 | Rustad et al. | 128/200.18 |
| 2005/0183718 A1 * | 8/2005 | Wuttke et al. | 128/200.14 |
| 2005/0205085 A1 * | 9/2005 | Blacker et al. | 128/200.21 |

FOREIGN PATENT DOCUMENTS

| | | |
|---|---|---|
| EP | 0 414 536 A2 | 2/1991 |
| EP | 0 587 380 B1 | 3/1993 |
| EP | 0 587 380 | 3/1994 |
| EP | 0 641 570 A1 | 3/1995 |
| EP | 0 711 609 A3 | 10/1996 |
| EP | 0 855 224 A2 | 7/1998 |
| EP | 0 938 906 A2 | 9/1999 |
| FR | 1 070 292 | 7/1954 |
| GB | 675 524 | 7/1952 |

* cited by examiner

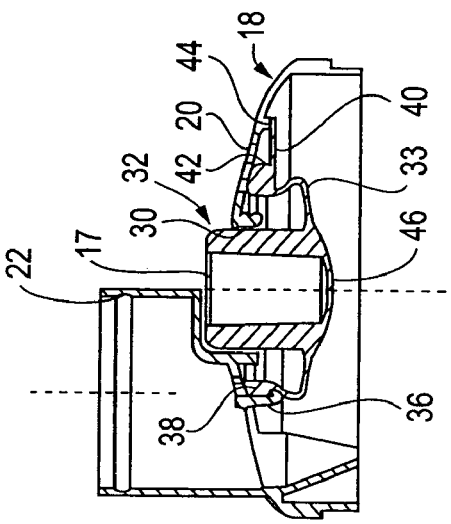
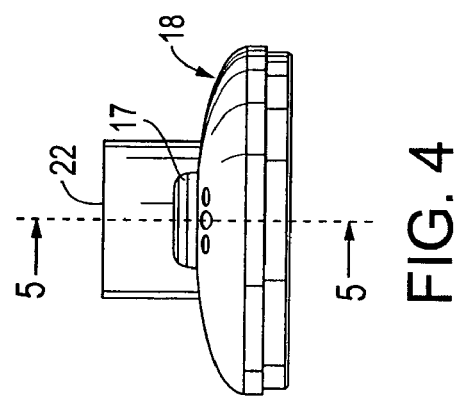
FIG. 4
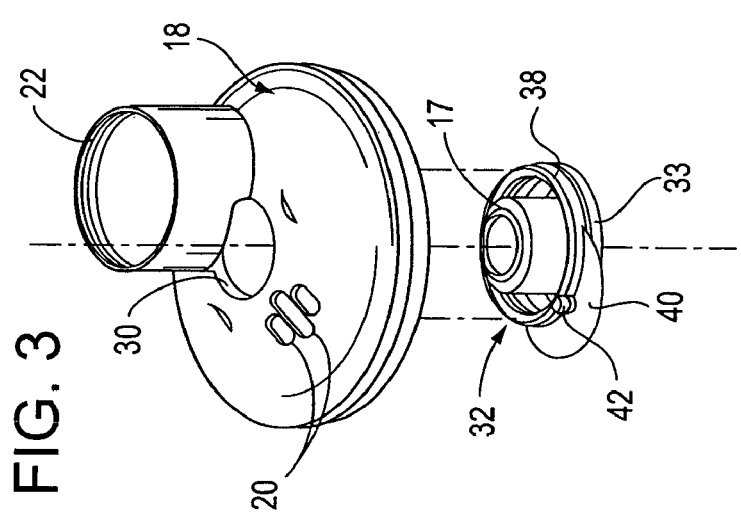
FIG. 3

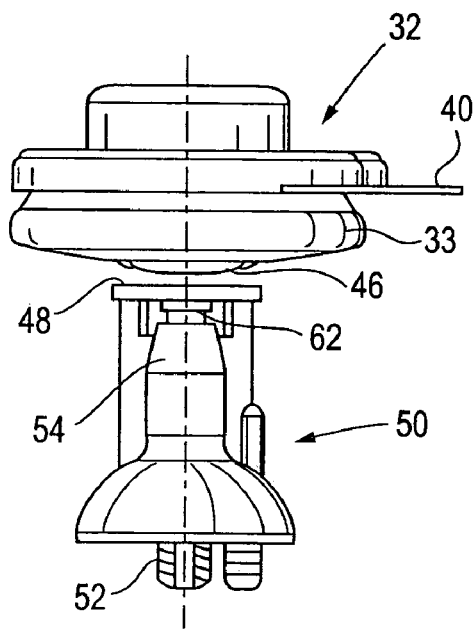
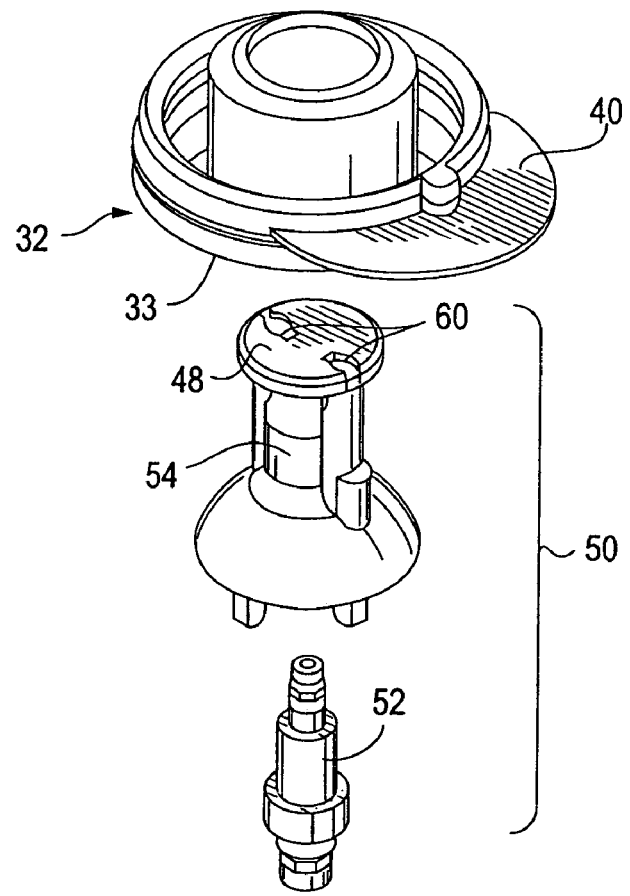
FIG. 6
FIG. 7

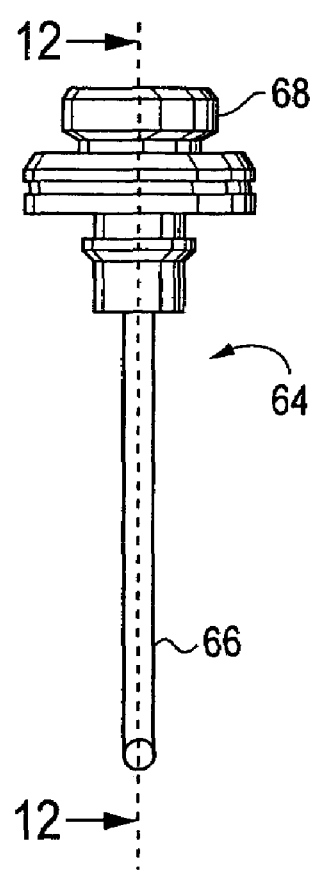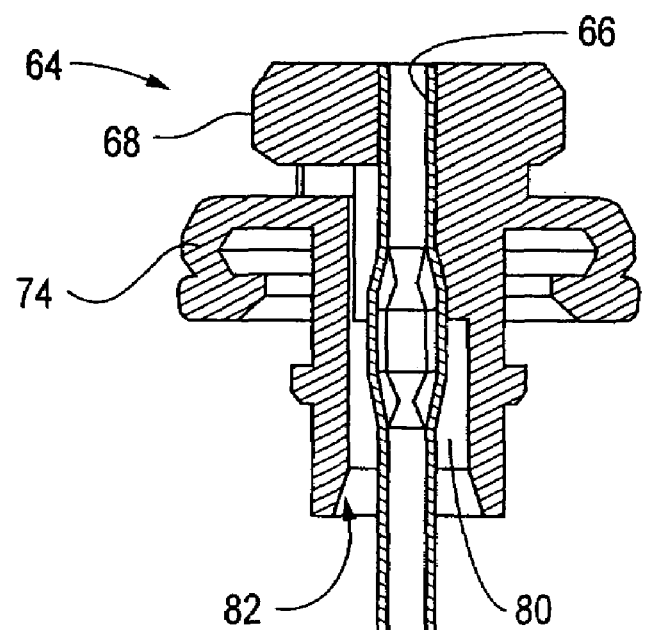

NEBULIZER APPARATUS AND METHOD

CROSS-REFERENCE TO RELATED APPLICATIONS

This application claims the benefit of U.S. Provisional Application Ser. No. 60/494,892, filed Aug. 13, 2003, pending, the entirety of which is incorporated herein by reference.

FIELD OF THE INVENTION

The present invention relates to an apparatus and method for generating an aerosol for delivery to a patient. More particularly, the present invention relates to a nebulizer configured to remove a fluid from a source of fluid and generate an aerosol in coordination with a patient's breathing. The present invention is also well suited for continuously generating an aerosol independent of a patient's breathing.

BACKGROUND

Medical nebulizers that nebulize a fluid into an aerosol for inhalation by a patient are well-known devices commonly used for the treatment of certain conditions and diseases. Nebulizers have applications for conscious, spontaneously breathing patients and for controlled, ventilated patients. As used in this specification, the term "patient" includes, without limitation, humans and animals.

In nebulizers, a diverter is primarily used to direct a gas across a liquid channel to create a venturi effect causing the liquid to be entrained into the gas stream. The term "diverter", as used in this specification, includes, without limitation, any baffle or impinger. As a result of the nebulization process described above, the fluid is transformed into an aerosol, that is, the fluid is caused to form small particles that are suspended in the air and that have a particle size in a range suitable for the intended therapy. A common therapy is inhalation therapy, whereby a patient inhales a medicated aerosol to treat an ailment, such as asthma.

Important considerations in the design of a nebulizer are the timing and dosage regulation of the aerosolized fluid. In some nebulizer designs, a continuous stream of pressurized gas entrains the fluid against the diverter to constantly generate an aerosol until the fluid in a reservoir is depleted. Continuous nebulization may result in a waste of aerosol, such as to the atmosphere, during a patient's exhalation or during a delay between inhalation and exhalation. The amount of wasted aerosol may be difficult to quantify and some of the aerosol may be lost to condensation on the nebulizer or mouthpiece, or to evaporation, during periods of non-inhalation. Nebulizers implementing a timed or non-continuous nebulization may adversely affect particle size and density as the nebulization is turned on and off.

Effective and economical nebulizer therapy includes the ability to quickly generate an aerosol within a desired particle size range. An effective nebulizer preferably provides these features synchronously with the inhalation of the patient. In order to actuate a mechanical nebulizer, a patient's inhalation effort must overcome certain variables. Depending on the structural configuration of the nebulizer, these variables may include one or more of the following: the volumetric flow rate of the flowing gas; air leaks in the device; the force exerted by the flowing gas on a moveable diverter; and the friction between moveable parts. The greater the flow rate, air leaks and friction, the greater the inhalation effort required in order to actuate the device. It is desirable that a nebulizer has adequate sensitivity to quickly respond to an inhalation while not adversely restricting the patient's inhalation.

Most nebulizer designs have difficulty delivering all of the medication that is placed in the nebulizer to the patient. The inefficiency in delivering the medication may stem from some of the medication sticking to the chamber walls of the nebulizer, structural issues in the nebulizer that prevent medication from reaching the desired destination, and other reasons. Failure to use all of the medication adds to the cost of aerosol delivery and can create uncertainty concerning the actual dosage of medication delivered to a patient. Accordingly, it is also desirable to have a nebulizer that is effective for efficiently delivering measured amounts of medication to a patient.

BRIEF SUMMARY

In order to address the deficiencies in the prior art, an improved nebulizer is discussed below. According to a first aspect of the invention, a nebulizer is provided having a housing with an air inlet, such as an ambient air inlet or an inlet designed to cooperate with a controlled source of air, and defining a chamber for holding an aerosol. An air outlet permits aerosol to be withdrawn from the chamber and an ambient air inlet allows a supply of air to enter the chamber. A pressurized gas inlet and an adjacent fluid orifice in the chamber cooperate to generate an aerosol when the nebulizer is actuated. A fluid return channel connected with the chamber and a fluid source generates a suction force when fluid is removed from fluid source during nebulization to assist in recovering condensed fluid moving down the wall of the chamber. In one embodiment, the fluid source may be a vial releasably attached to the nebulizer. In other embodiments, a fluid channel air inlet valve is movably disposed across a fluid channel air inlet to control actuation by opening and closing a fluid channel air inlet in communication with the fluid orifice.

According to other aspects of the invention, a nebulizer may be constructed with an aerosolization chamber having a first diameter in a plane substantially co-planar with an aerosolization plane in which the majority of aerosol is generated within the chamber, and a second diameter in a plane other than the aerosolization plane, where the first diameter is greater than the second diameter. The impaction of the aerosol against the chamber walls may be reduced, and aerosol particle size distribution improved, with a larger chamber area where the aerosol is generated. In alternative embodiments, the chamber may have curved or angled walls tapering in at the bottom of the chamber, or at both the top and bottom of the chamber.

In yet other aspects of the invention, a nebulizer system is disclosed. The nebulizer system includes a vial containing a fluid for nebulization and a nebulizer for releasably engaging the vial and nebulizing the fluid in the vial. The nebulizer consists of a housing having an ambient air inlet, a chamber for holding an aerosol and an air outlet communicating with the chamber so that the aerosol may be withdrawn from the chamber. A pressurized gas inlet is adjacent a fluid orifice in the chamber and the fluid orifice in communication with a fluid channel. The pressurized gas inlet may be a cone-shaped gas nozzle with a fluid nozzle coaxially positioned as cone-shaped sleeve around it. A skirt portion extends radially outward from the cone-shaped fluid nozzle and reaches substantially to an inner wall of the chamber. A fluid reclamation opening is defined by the inner wall of the chamber and the outer edge of the skirt portion. A fluid channel air inlet valve is movably disposed across a fluid channel air inlet so as to control actuation of the nebulizer. A fluid return channel is in communication with the fluid reclamation opening and a fluid return opening in the vial so that a suction force generated by removal of fluid from the vial into the nebulizer during nebulization assists in recovering condensed fluid on a wall of the chamber. In one embodiment, the fluid return channel and a fluid supply channel are separate from one another.

As used in this specification, the term "fluid orifice" means either the fluid inlet or the fluid outlet and may be used interchangeably with these terms. Additionally, the ambient air inlet valve may be used to alleviate inhalation effort after an initial period of inhalation. The diverter may also be movable relative to the nebulizer housing, and movably or fixedly positioned relative to either the pressurized gas orifice or fluid orifice. In yet other embodiments the fluid channel air inlet valve may be a mushroom valve. The fluid channel air inlet may be integrally formed out of a single piece of material that also forms the diverter and fluid nozzle for the nebulizer. Other embodiments may include anti-spill structures in the chamber to prevent spillage of fluid when the nebulizer is inadvertently left on its side or knocked over. Further aspects and advantages of the invention are discussed below in conjunction with the preferred embodiments.

BRIEF DESCRIPTION OF THE DRAWINGS

FIG. 3 is an exploded perspective view of a cover and valve assembly suitable for use in the nebulizer of FIGS. 1 and 2.

FIG. 4 is a side view of the assembled cover and mushroom valve assembly of FIG. 3.

FIG. 5 is a cross-sectional view taken along line 5-5 of FIG. 4.

FIG. 6 is a side view of a valve assembly and nozzle assembly suitable for use in the nebulizer of FIGS. 1-2.

FIG. 7 is an exploded perspective view of the valve assembly and nozzle assembly of FIG. 6.

FIG. 11 is a side view of the handle seal assembly shown in the nebulizer of FIGS. 9-10.

FIG. 12 is a cross-sectional view of the handle seal assembly of FIG. 11 taken along line 12-12.

DETAILED DESCRIPTION OF THE PRESENTLY PREFERRED EMBODIMENTS

Figure 1:
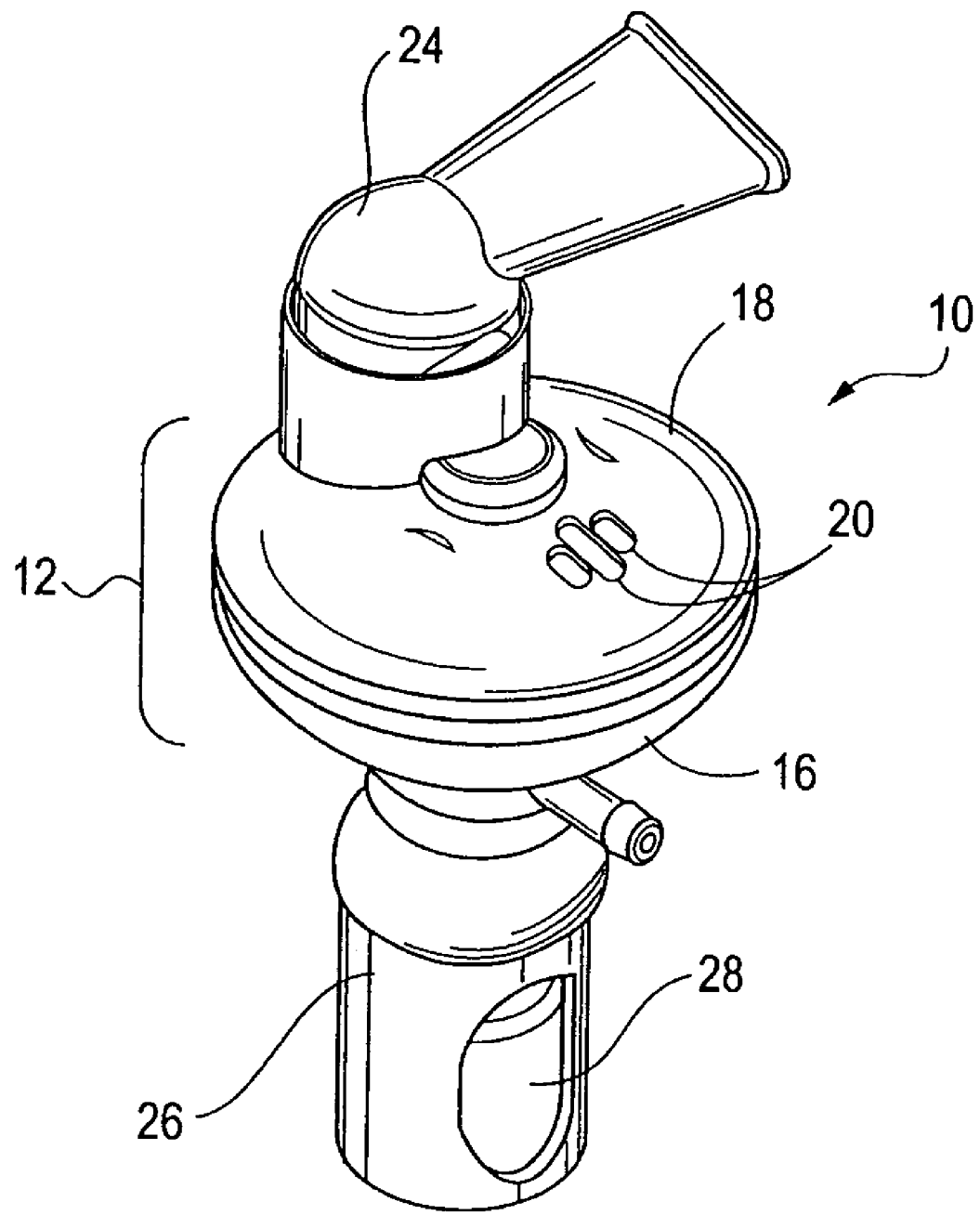
FIG. 1 is perspective view of a nebulizer according to one embodiment of the present invention.
Figure 2:
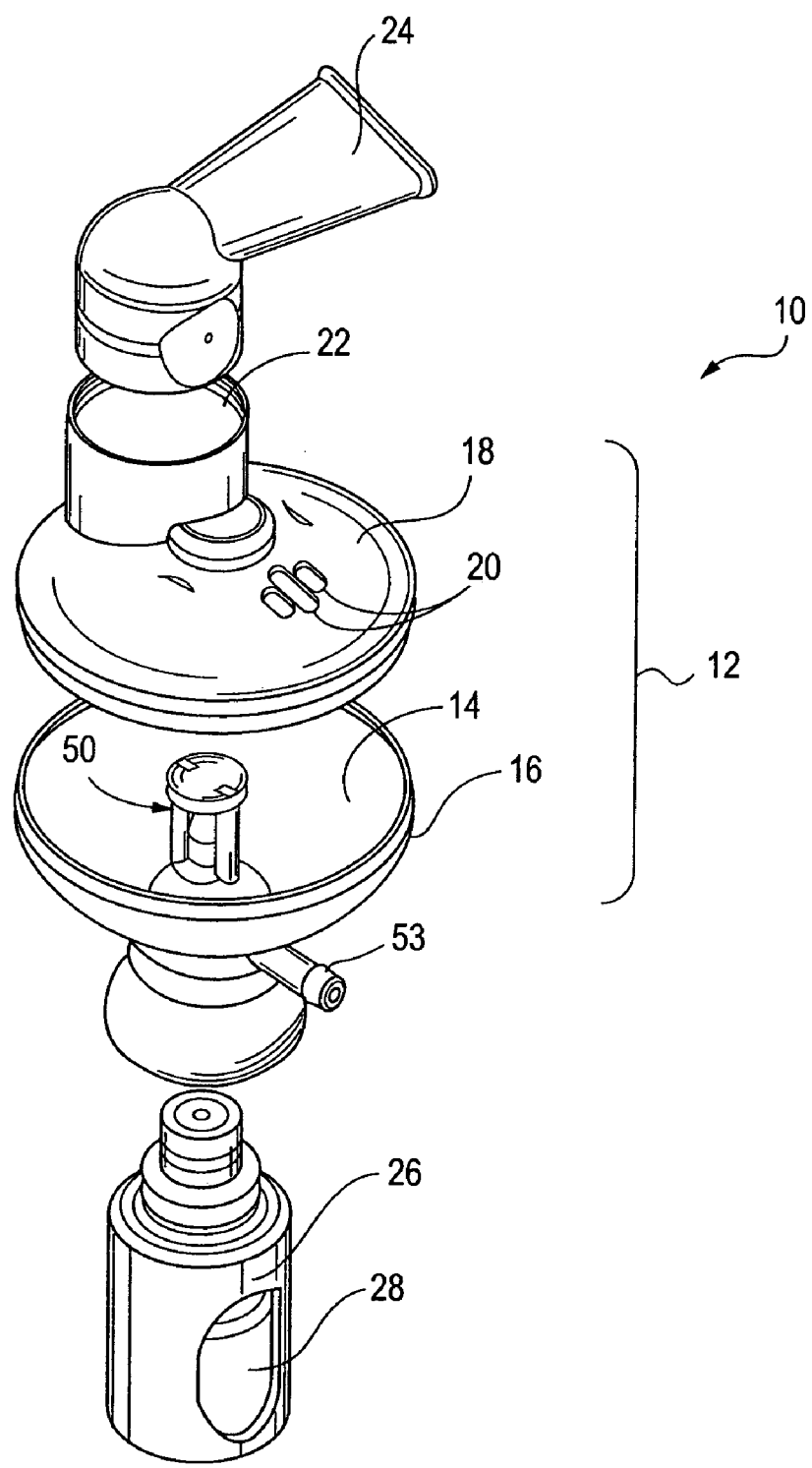
FIG. 2 is an exploded perspective view of the nebulizer of FIG. 1.

An embodiment of a nebulizer 10 for nebulizing a fluid drawn from a vial connected to the nebulizer is shown in FIGS. 1-2. As used in this specification, the term "fluid" includes, without limitation, a fluid comprising a medicine, whether in the form of an emulsion, suspension or solution that can be nebulized into an aerosol.

The nebulizer 10 includes a housing 12 consisting of a base 16 that is removably attachable with a cover 18. The interior of the base and cover is hollow and defines a chamber 14 that is suited to receive an aerosol. The chamber 14 may be any number of shapes and preferably is angled or curved inward towards its bottom so that any aerosol that impacts the interior wall of the chamber 14 will condense and be drawn toward the bottom of the chamber 14. An air inlet 20, comprised of one or more openings in the cover 18, permits air to be drawn into the chamber 14. An air outlet 22 extends through the cover 18. In one embodiment, the air outlet 22 is offset from the central vertical axis of the housing 12. The air outlet 22 on the cover 18 is sized to cooperate with a removable, rotatable mouthpiece 24 through which a patient may withdraw an aerosolized fluid from the chamber 14. The rotatable mouthpiece 24 is adjustable to an orientation convenient to the patient. A handle section 26 is removably detachable from the base 16 and is sized to receive a vial 28 or ampoule containing a fluid to be nebulized.

The housing, cover and handle section may be manufactured using any of a number of materials and manufacturing processes. For example, in one embodiment the housing, cover and handle section may each be constructed of a material formed by an injection molding process. Suitable materials include a plastic material, such as polypropylene, polycarbonate or a polycarbonate blend, or a metal material. The housing, cover and handle section may each be made of the same or different materials.

An aerosol actuator opening 30 is defined by the cover 18 and is sized to receive a button 17 connected with, or integrally formed with, a fluid channel air inlet valve assembly 32 mounted to the cover 18 and positioned inside the chamber 14. In one embodiment, the aerosol actuator opening 30 is located on the central vertical axis of the housing 12 when the base 16 and cover 18 are assembled. As best shown in FIGS. 3-5, the button 17 may be an integral part of the fluid channel air inlet valve assembly 32. In the embodiment of FIGS. 3-5, the valve assembly 32 may be a mushroom valve that attaches to the cover 18 by a frictional fit or snap-fit between locking ring 36 inside the cover and a locking ledge 38 formed in the outer edge of the valve assembly. The locking ledge 38 is connected to the central portion of the assembly 32 by an integrally formed, flexible rolling membrane 33.

In one embodiment, the valve assembly 32 includes an inhalation valve 40 formed integrally along an edge of the locking edge 38. An alignment tab 42 on the locking ledge 38 ensures proper orientation of the valve assembly with the cover 18 so that the inhalation valve 40 will be properly aligned during assembly to cover the air inlet openings 20 and form a seal with sealing ring 44 on the underside of the cover 18. The inhalation valve 40 is preferably constructed of a flap of flexible material having a thickness designed to flex inwardly in response to a desired negative pressure in the chamber. The valve assembly may be constructed from an elastomer, such as silicone or rubber. In one embodiment, the inhalation valve 40 may have a thickness of about 0.02 inches.

Figure 8:
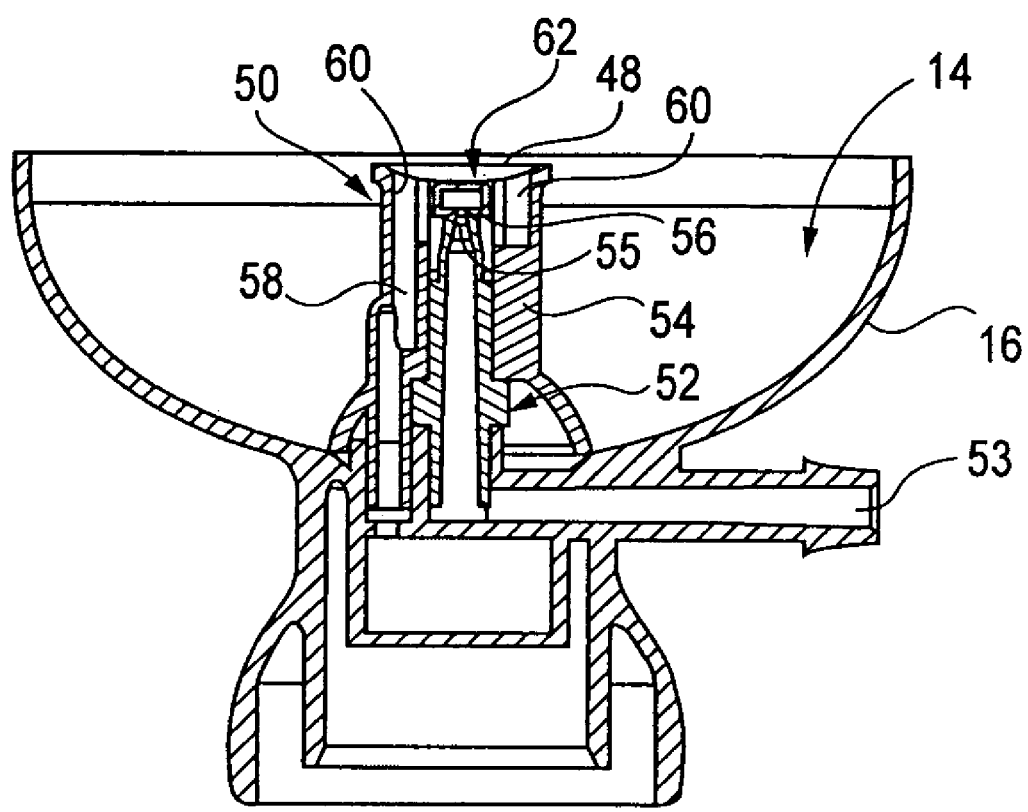
FIG. 8 is a cross-sectional view of the base and nozzle assembly of FIGS. 1-2.

The rounded bottom portion 46 of the valve assembly 32 is configured to engage a valve seat 48 positioned in the chamber. As shown in FIGS. 6 and 7, the valve seat 48 is connected with a nozzle assembly 50 consisting of a gas nozzle 52 and a fluid nozzle 54. The gas nozzle 52 receives a pressurized gas from a gas inlet 53 extending from the base and directs the received gas through a gas orifice in the chamber, as illustrated in FIG. 8. The fluid nozzle 54 guides fluid from the ampoule 28 in the handle 26 to a fluid orifice 56 in the chamber. In the embodiment of FIGS. 6-8, the fluid nozzle 54 fits over the gas nozzle 52 and a separate fluid channel 58 extends down through to the lower portion of the fluid nozzle and out through the base 16. Near the fluid orifice 56, the fluid channel emerges through the inner diameter of the fluid nozzle and the outer portion of the gas nozzle forms part of the fluid channel so that the fluid orifice is substantially annular.

In other embodiments, there may be one or more fluid channels. The fluid channel may be formed by a space between the fluid and gas nozzles, one or more grooves along the inside of the fluid nozzle and/or the outside of the gas nozzle, or channels within the wall of the gas or liquid nozzles. The fluid channel 58 communicates with the fluid orifice 56 and at least one fluid channel air inlet 60 in the valve seat 48. As explained in greater detail below, the fluid channel air inlet 60 positioned inside the chamber 14 on the nozzle assembly cooperates with the bottom portion 46 of the valve assembly 32 to open and close the fluid channel air inlet 60 synchronously with a patient's breathing, or in response manual actuation by physical contact against the button on the outside of the valve assembly and extending through the cover of the nebulizer. In one embodiment, the valve assembly is constructed of a flexible rubber material. Although individual valves for the air inlet and fluid channel air inlet may be fabricated separately on separate pieces of flexible material, or the valves may each be constructed from other individual components, the valve assembly 32 is preferably a one-piece, integrated construction reducing the part count and cost of manufacturing and assembly. An example of a fluid channel air inlet configuration used in a nebulizer is seen in U.S. application Ser. No. 10/306,886, filed Nov. 27, 2002, which published on Jul. 24, 2003 as U.S. 2003/0136399 A1, the entirety of which is hereby incorporated herein by reference.

In the embodiment illustrated in FIGS. 6-8 the fluid orifice 56 and gas orifice 55 are coaxially aligned and face a diverter 62 that is spaced at a fixed distance from the fluid and gas orifices. In one embodiment, the outer diameter of the tip of the gas nozzle is approximately 2.0 millimeters (mm), the inner diameter of the tip of the fluid nozzle is approximately 2.4 mm and the fixed gap between the diverter and the fluid and gas orifices is approximately 1.0 mm. Other diameters and dimensions may also be used. Although a single annular fluid orifice 56 is shown, embodiments where the fluid outlet has other shapes, or comprises more than one discrete orifice positioned adjacent the pressurized gas orifice, are also contemplated. The non-moveable diverter 62 directs the gas exiting the gas orifice across the fluid orifice to create a venturi effect, thereby causing the fluid to be entrained into the gas stream to create an aerosol. Preferably, the diverter is attached to, or integrally molded with, the fluid nozzle 54. Alternatively, the diverter may be connected to the inside of the nebulizer 10.

The diverter 62 has a flat surface having a predetermined area and is positioned at a fixed distance from the gas orifice 55. The diameter of the gas orifice may be varied, but, in combination with the other nebulizer dimensions provided below for one embodiment, may be approximately 0.56 mm. In this example, the distance between the diverter and nozzle is in the range of about 0.8 mm to 1.2 mm, and most preferably 1.0 mm, and the diameter of the diverter is approximately 4.0 mm. These dimensions may be varied to achieve a desired particle size and aerosolization as is known to those of skill in the art. The surface of the diverter is also preferably aligned parallel to the surface of the tip of the gas nozzle 52 and perpendicular to the flow of pressurized gas through the gas orifice 55. Other diverter embodiments may also be implemented. For example, in other embodiments, a diverter with a wedge shape, curved or other non-perpendicular orientation may be used.

Referring again to FIGS. 6-8, the fluid channel air inlet 60 is positioned in the valve seat 48 and aligned below the bottom portion 46 of the valve assembly 32. On inhalation through the mouthpiece, the negative pressure in the chamber causes the membrane 33 to flex and bring the bottom portion 46 of the valve 32 against the valve seat 48 to substantially seal of the one or more openings of the fluid channel air inlet 60.

Once substantially sealed, the gas exiting the gas orifice 55 and deflected by the deflector 62 over the fluid orifice 56 can create the suction necessary to entrain the fluid up the fluid channel into the path of the pressurized gas causing the fluid and gas to mix resulting in an aerosol with the desired particle size characteristics. The flexible membrane 33 of the valve assembly is preferably very sensitive to pressure changes and, therefore, can be triggered at low flows making the apparatus suitable for children and the elderly who typically have low rates of inhalation. Further, the valve assembly has a button portion extending through the cover that can be manually depressed. Accordingly, the patient or the caregiver can manually actuate the apparatus by pressing the button portion to position the bottom portion 46 in the valve seat 48.

In one embodiment, the opening of the fluid orifice 56 and the openings of the fluid channel air inlets 60 in the valve seat 48 are sized such that the deflected gas passing over the fluid orifice maintains a negative (suction) pressure of (e.g. 1-2 cm $H_2O$) over the liquid channel. Thus, while not sufficient to raise the fluid all the way to the fluid orifice and permit nebulization, the fluid is partially drawn up the fluid channel by the pressure so that the fluid has only a short distance to travel when the fluid channel air inlets 60 are closed by the valve 32 seating in the valve seat 48. This negative pressure can help reduce response time by lessening the distance that a fluid must travel to reach the fluid orifice after the fluid channel air inlets are closed when the nebulizer is actuated through breath actuation, or manual movement, of the valve assembly 32.

In one embodiment the fluid channel air inlet valve 32 is configured to deflect over a gap G, in the range of 1.0-3.0 mm, and most preferably approximately 2.0 mm, before it blocks the end of the fluid channel air inlet. Other gap distances may be used with variations in the parameters of the membrane, geometry and diameter, and variation in other aspects of the nebulizer such as fluid channel air inlet. In this embodiment, the fluid channel air inlet valve is designed to respond to a negative pressure of approximately 0.5-1.0 cm $H_2O$ to achieve this deflection. The thickness of the membrane may be approximately 0.2 mm. Other gap distances G, and geometries, may be utilized in other embodiments.

Figure 9:
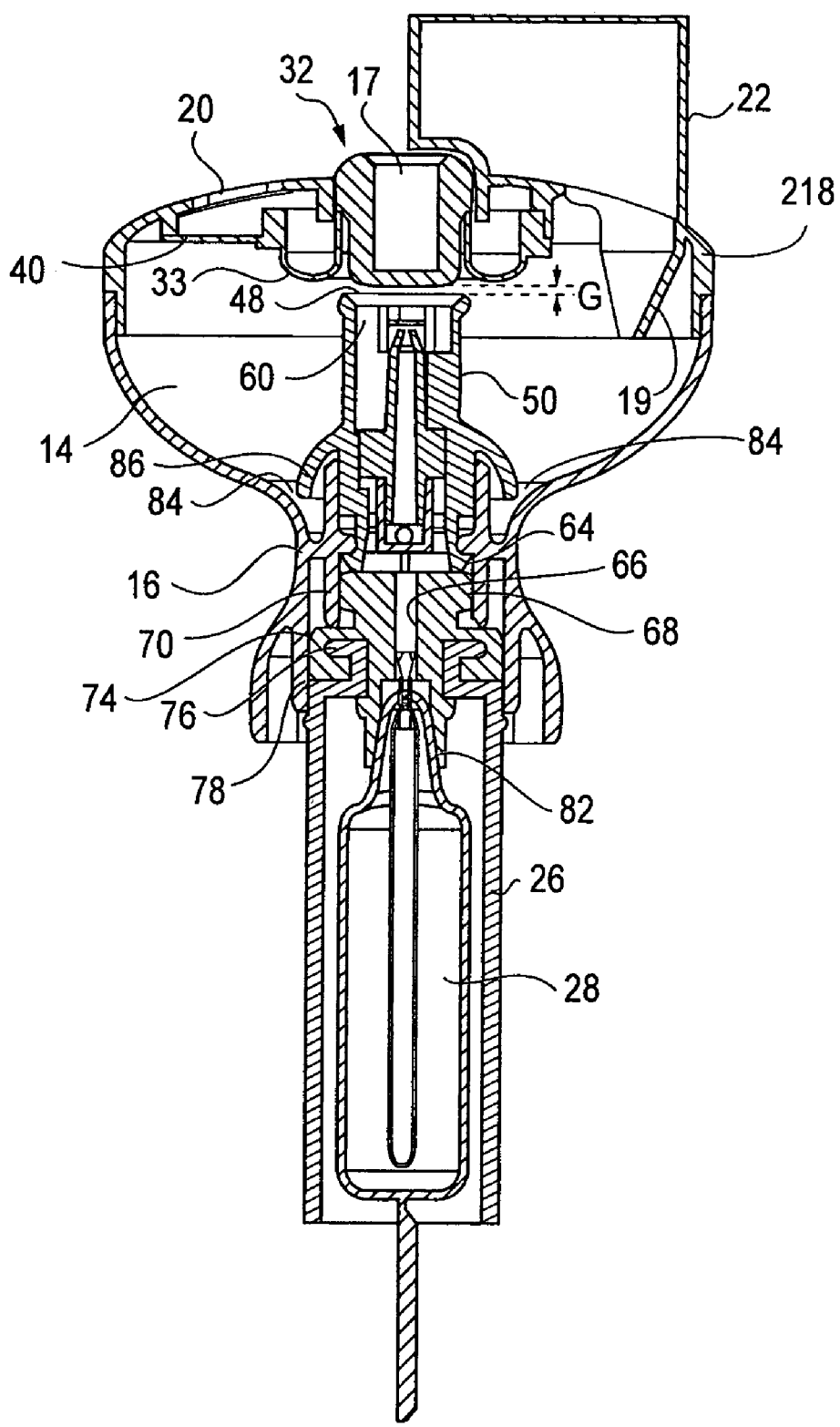
FIG. 9 is a cross-sectional view of a nebulizer including handle with vial according to one embodiment.
Figure 10:
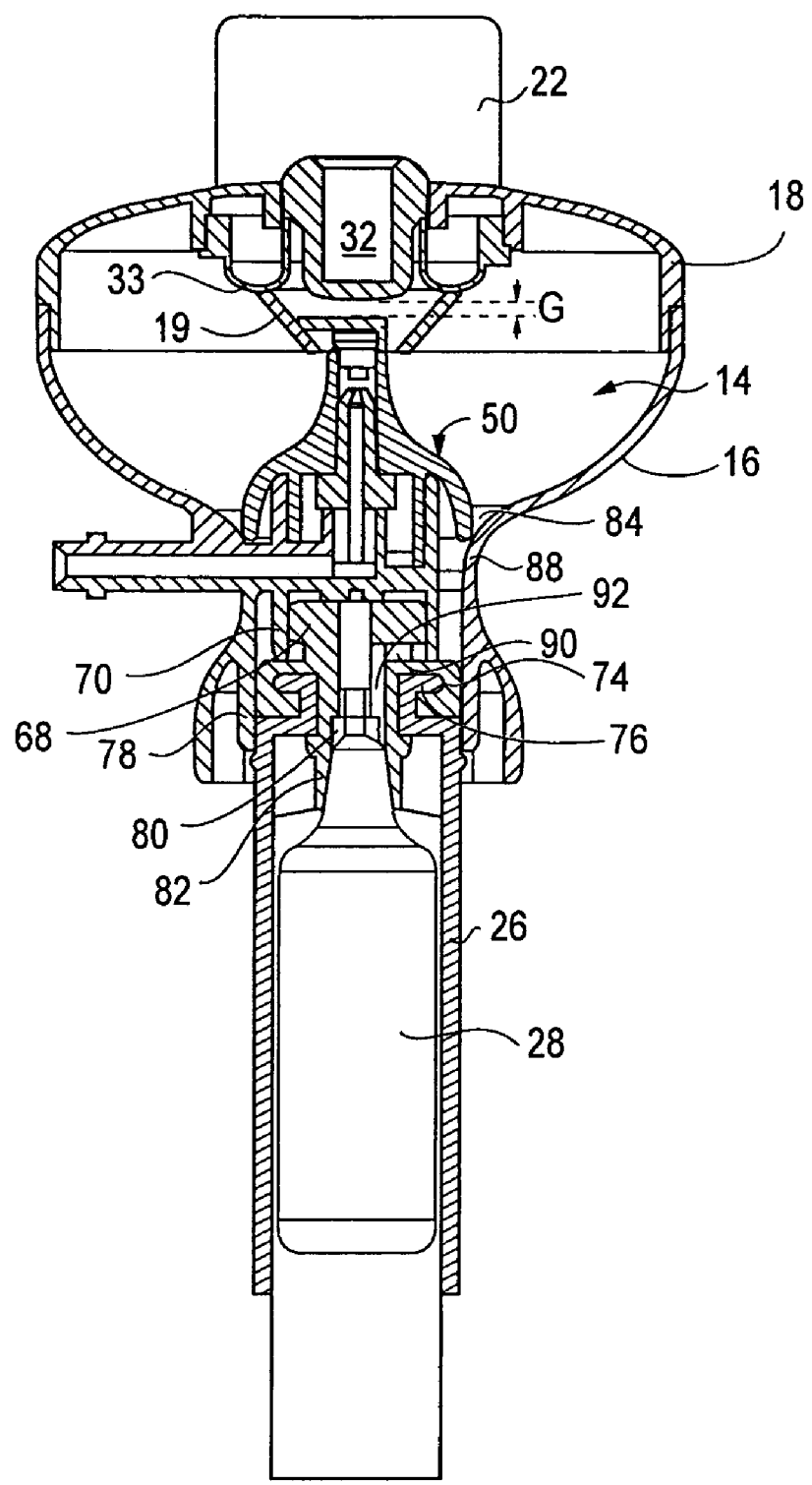
FIG. 10 is an alternate cross-sectional view of the nebulizer of FIG. 9.

FIGS. 9-10 best illustrate the fluid supply and return mechanisms for the nebulizer 10. In one embodiment, the vial 28 containing a medicament in fluid form, and the handle containing the vial therein, connect with the base 16 via a handle seal assembly 64. As shown in FIGS. 8 and 11-12, a handle seal assembly 64 also contains a hollow needle 66 extending through the handle seal assembly 64 for puncturing the vial and providing a path for the fluid to be drawn into the fluid channel 58 of the nozzle assembly 50. The upper portion of the handle seal assembly 64 includes a base seal portion 68 that frictionally fits into a base seal wall 70 protruding from the bottom of the base 16. A circumferential lip 74 spaced away from the base seal 68 performs a dual function of gripping a complimentary shaped flange 76 surrounding the opening at the top portion of the handle 26 along the inner diameter of the lip 74, and acting as a seal against the handle seal wall 78 extending downward from the bottom of the base 16. A central portion of the handle seal assembly 64 extends through the opening at the top of the handle and defines a vial receiving area 80 recessed in the end of the handle seal assembly 64. The walls of the vial receiving area 80 frictionally fit over the top of the vial to form a vial opening seal 82.

Figure 13:
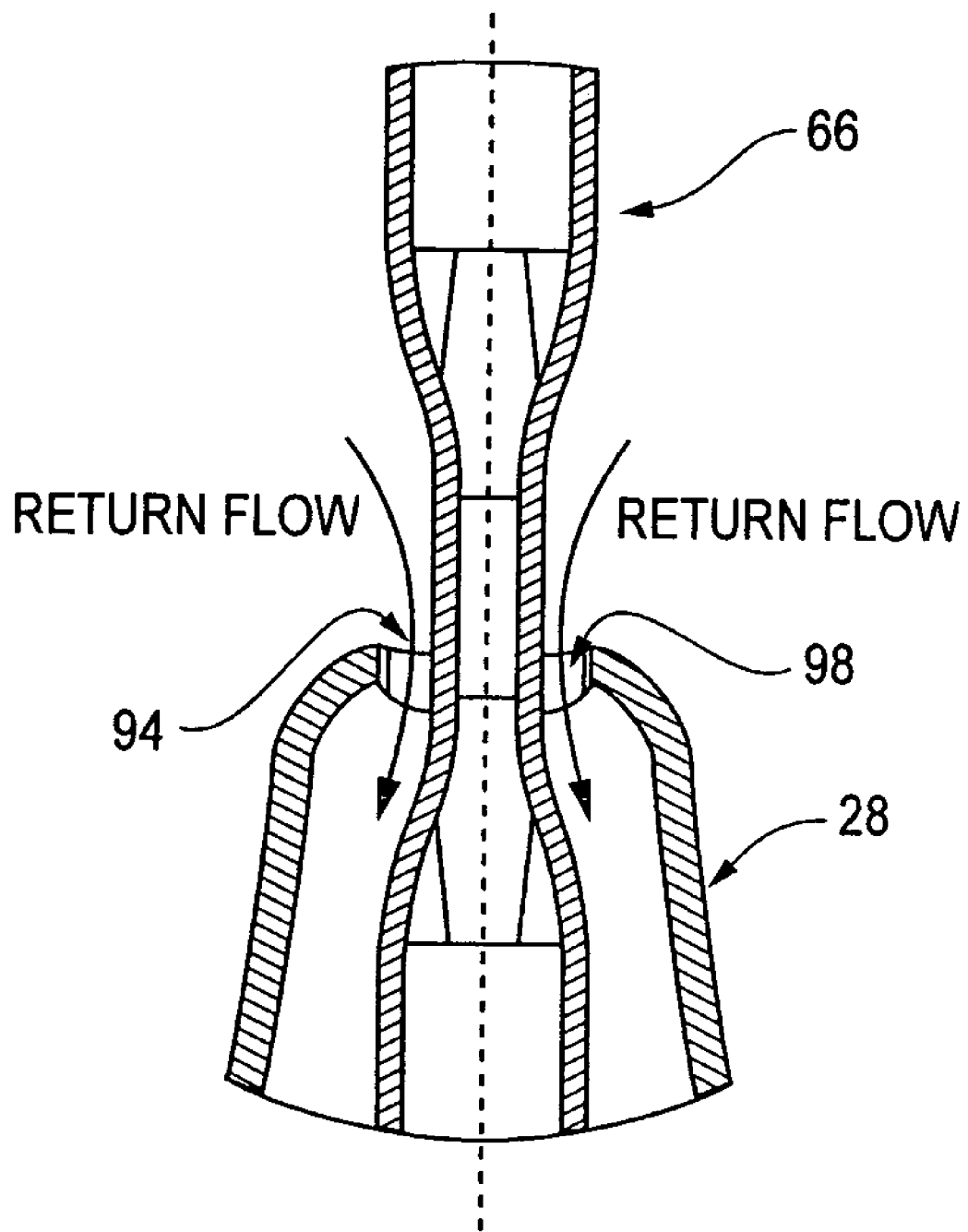
FIG. 13 is a partial cross-sectional view of the needle portion of the handle seal assembly inserted into a vial.

To permit efficient use of fluid contained in the vial 28, fluid that condenses on the wall of the chamber 14 is provided a path down the wall through a return opening 84 defined by the gap between the lower portion of the skirt 86 at the base of the nozzle assembly 50 and chamber wall. The fluid return path 88 extends down through the edge of the base between the base seal wall 70 and the outer wall of the base 16. The fluid return path 88 continues to a return fluid opening 90 in the handle seal assembly 64 between the base seal 68 and the upper portion of the circumferential lip 74 of the handle seal assembly. The fluid return opening extends radially inward in the handle seal assembly to the outer wall of the needle 66 and a handle return channel 92 continues longitudinally along the outer wall of the needle 66 and inner wall of the handle seal assembly 64 until it reaches the vial receiving area 80 where the needle 66 pierces an opening in the top of the vial 28. The vial opening seal 82 prevents any returned fluid from escaping. The fluid returning to the mouth of the vial reenters the vial through a gap in the opening of the vial created by cooperation between the circular cross section of the lower portion of the hollow needle 66 and the indented portion 94 of the needle that is positioned to straddle the opening of the vial 28 when the vial is fully inserted, as shown in FIG. 13. An advantage of this configuration is the presence of separate fluid supply and return paths that allow a suction-assist to be used on the fluid return path. Also, air is permitted to enter the vial when fluid is removed so that restrictions on fluid flow from the vial, that might otherwise occur if a vacuum was allowed to form in the vial when fluid is removed, are avoided.

Figure 14:
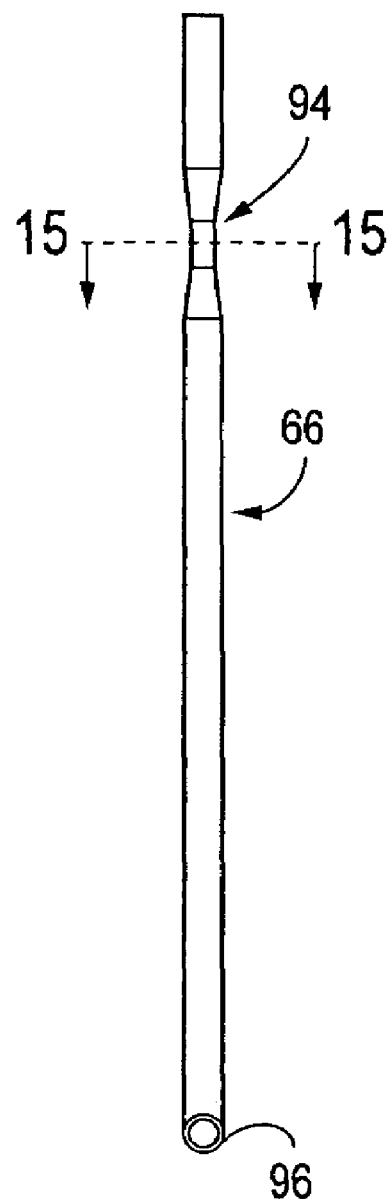
FIG. 14 is a side view of the needle portion of the handle seal assembly of FIG. 12.
Figure 15:
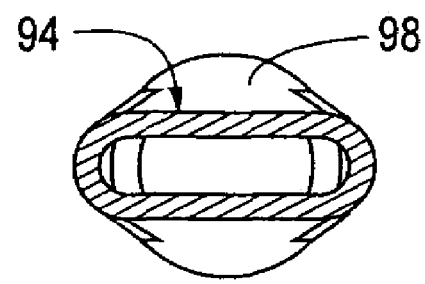
FIG. 15 is a cross-sectional view of the indented section of the needle of FIG. 12 taken along line 15-15.
Figure 16:
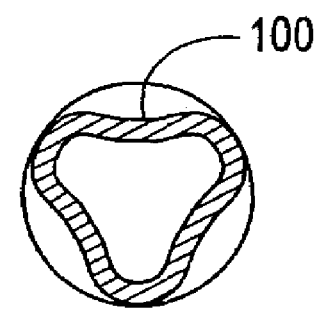
FIG. 16 is a cross-sectional view of an alternative embodiment of the indented needle section of FIG. 15.

As best shown in FIGS. 13-15, the indented portion 94 of the needle provides a cross section that differs from the circular cross section of the lower portion of the needle 66. After the beveled edge 96 of the needle punctures the foil or other covering at the top of the vial 28, the circular cross section of the lower portion of the needle passes through the opening and, when the indented portion 94 properly straddles the opening, a gap 98 is left between the circular cross section of the punctured vial opening and the flattened wall of the indented portion 94 (FIG. 15). As illustrated by the alternative embodiment in FIG. 16, any of a variety of other shapes of indented portions 100 may be used to achieve a gap between the needle and the opening in the top of the vial suitable for allowing fluid to return into the vial. Although an indented portion is described with the needle having a lower portion with a generally circular cross section, any of a number of cross sections for the lower portion and indented portion may be used such that a gap between the opening in the vial made by the cross section of the lower portion is formed.

Turning to the operation of supplying fluid from the vial 28 to the fluid orifice 56 during nebulization, the beveled end 96 of the needle 66 is configured to reach substantially to the bottom of the vial 28 to reduce the amount of fluid left behind in the vial 28. Fluid drawn from the vial travels through the needle 66 out through the top of the handle seal assembly 64 and up through the fluid channel 58 in the fluid nozzle 54. The fluid is drawn through the fluid nozzle to the fluid orifice and, as fluid is drawn out through the fluid orifice into the stream of pressurized gas, the fluid is nebulized.

Figure 17:
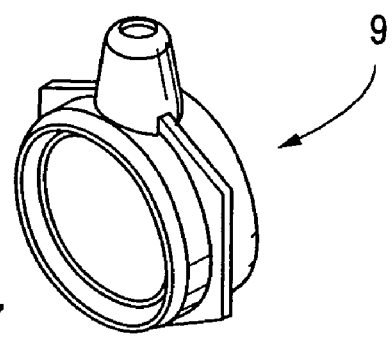
FIG. 17 is a perspective view of an alternative vial usable with an embodiment of the nebulizer.
Figure 18:
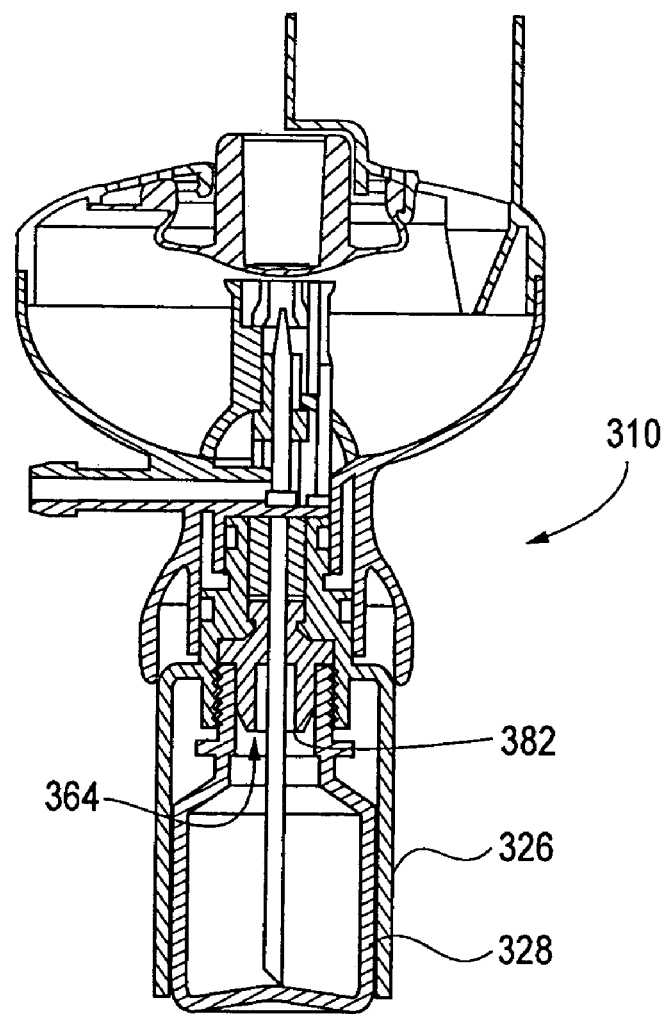
FIG. 18 is a cross-sectional view of an alternative embodiment of the nebulizer of FIGS. 9-10.

The vial may be of any of a number of standard fluid dispensing vials used to carry measured portions of, for example, liquid medication. As shown in FIGS. 9-10, the vial 28 may be a cylindrically shaped vial with a foil or other membrane/diaphragm capable of being pierced by a needle. Other shapes and types of vials also may be used, for example a PULMICORT ampoule 9 as shown in FIG. 17. Although the vials may use a membrane or foil sized to cooperate with the needle 66 of the handle seal assembly 64 to permit the needle to puncture the membrane, the nebulizer may be modified to connect with vials that do not have foil or other membranes. As shown in FIG. 18, an alternative embodiment of the nebulizer of FIGS. 9-10 is shown where a threadable Albuterol bottle 328 is connected to the nebulizer 310. The handle portion 326 and handle seal assembly 364 have been modified to cooperate with the Albuterol bottle 328, however the remainder of the nebulizer is similar to that of the embodiment of FIGS. 9-10. The handle portion 326 is threadably connectable with the threads on the Albuterol bottle. In place of a needle with a varied cross-section used to pierce a membrane, the embodiment of FIG. 18 includes a handle seal assembly 364 where the vial opening seal 382 seals against the inner diameter of the bottle opening and the needle 360 has a uniform cross-section. Any of the vials and bottles discussed herein may be single-use, disposable vials or reusable vials suitable for sterilization, refilling and resealing.

Figure 32:
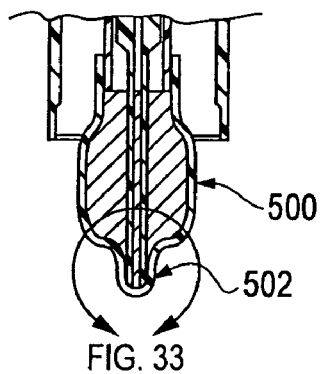
FIG. 32 is a cross-sectional view of an alternative vial configuration attached to a nebulizer.
Figure 33:
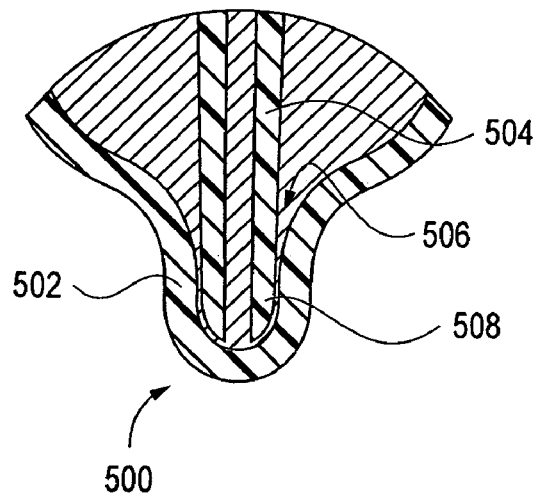
FIG. 33 is a sectional view of the vial of FIG. 32 taken along line B of FIG. 32.

In one alternative embodiment, as shown in FIGS. 32-33, the vial 500 may have a configuration to further reduce the residual volume of fluid left over in the vial. A nipple 502 in the base of the vial 500 may be fabricated to provide a small cavity 506 surrounding the end 508 of the needle 504 or other tubular member that has been inserted into the vial. The narrow gap around the needle allows for a very small volume of fluid to completely enclose the opening at the end of the needle. In one preferred embodiment, the shape of the nipple 502 is substantially the same as the shape of the end 508 of the needle 504. An advantage of this vial configuration is that the volume needed in the vial to provide sufficient fluid for nebulization may be reduced, thus improving fluid pick-up and minimizing the sputtering that can occur when air and fluid are both drawn into the needle.

The vial 500 may have a threaded, friction fit or other fastening arrangement at its opening to allow it to be removably attached to a nebulizer or fluid channel in communication with a nebulizer. Other than the small cavity formed in the bottom of the vial for the nipple 502, the vial may have any of a number of shapes. The vial 500 may be constructed of any number of materials suitable for holding a fluid. In one embodiment, it is contemplated that the vial may be made of a blow molded, or injection molded, plastic. The plastic may be a rigid plastic, or a flexible plastic that allows the vial to be squeezed. Although different dimensions may be fabricated based on the type of needle or tube and the type of fluid used, in one embodiment the gap between the needle and the inner wall of the nipple may be less than 0.026 inches and the inner diameter of the needle may be less than 0.51 inches.

The vial 500 of FIGS. 32-33 may be used with the nebulizer embodiments described herein or with any other nebulizer that can accommodate a vial. It is contemplated that the vial may be used with nebulizers utilizing breath-actuating mechanisms or continuous nebulization mechanisms, with or without fluid return channels. Suitable breath actuation mechanisms are disclosed in U.S. Pat. Nos. 5,823,179 and 6,044,841, and the entirety of each of these patents is incorporated herein by reference. Additional nebulizers with breath actuation mechanisms are disclosed in U.S. 2002/0157663 A1 to Blacker et al. and U.S. 2003/0136399 A1 to Foley et al., and the entirety of each of these applications is incorporated herein by reference.

Figure 19:
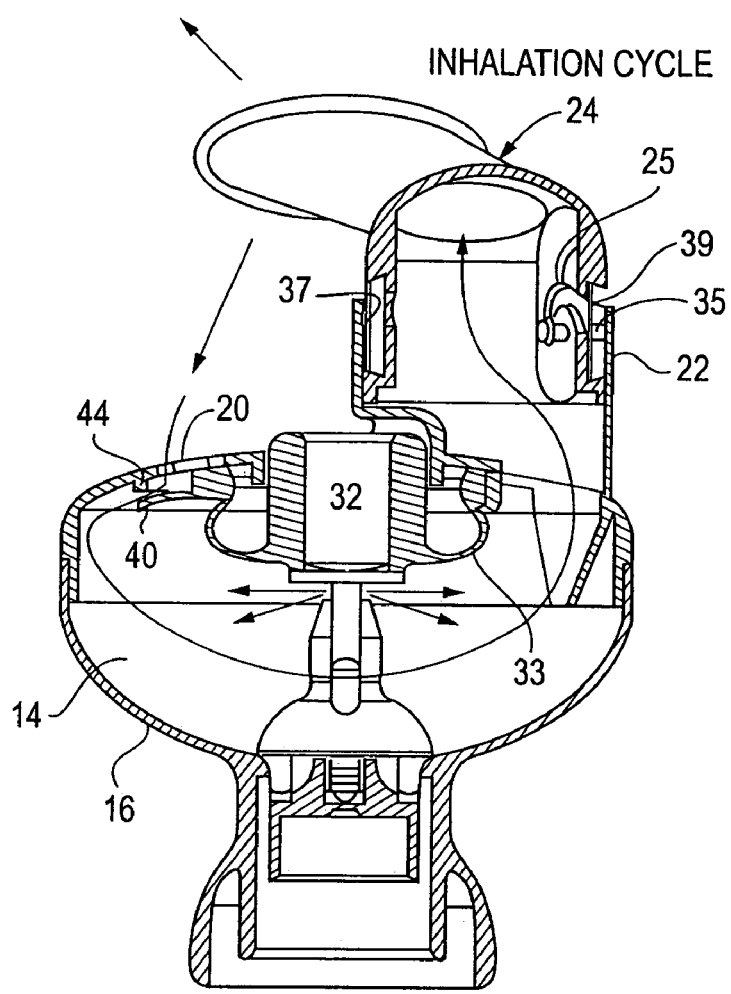
FIG. 19 is cross-sectional view of a nebulizer as in FIG. 1 in an actuated position.
Figure 20:
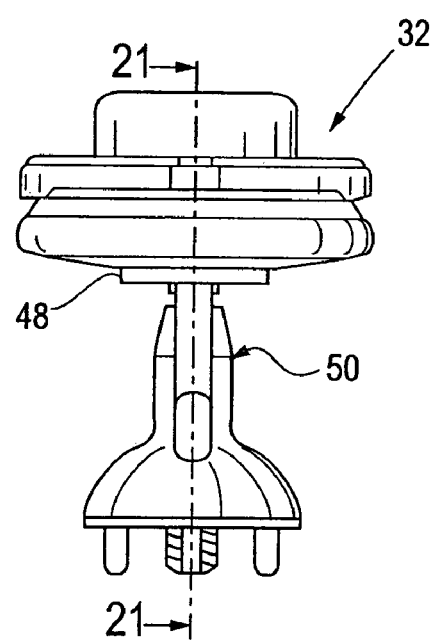
FIG. 20 is a side view of the valve assembly and nozzle assembly orientation at the start of nebulization.
Figure 21:
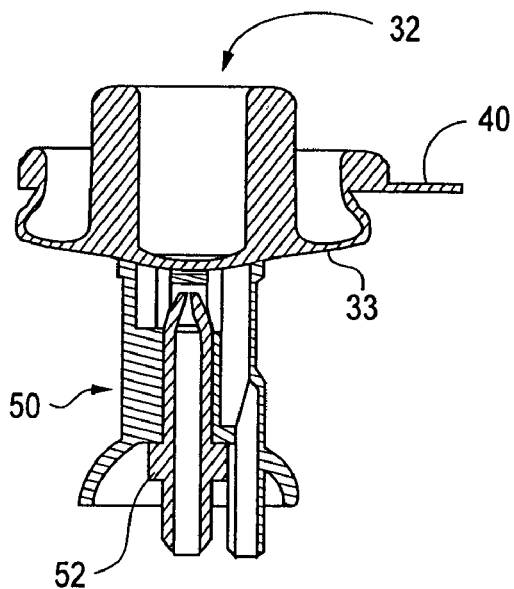
FIG. 21 is a cross-sectional view taken along lines 21-21 of FIG. 20.

FIGS. 19-21 illustrate the interaction of the nozzle assembly and the valve assembly during an inhalation cycle. As a patient inhales through the mouthpiece 24, the one-way, exhalation valves in the mouthpiece remain sealed and negative pressure in the chamber causes the membrane 33 of the valve assembly 32 to flex and draw in the bottom portion 46 until it seats in the valve seat 48, sealing shut the openings of the fluid channel air inlet 60. The gas being continuously supplied to the nebulizer via the gas nozzle and deflected over the fluid orifice will then be able to create sufficient suction in the fluid channel to draw fluid from the vial up the channel and into the stream of gas. The fluid is then nebulized in the gas stream deflected by the diverter 62 and is radially sent out from the nozzle assembly into the chamber. Shortly after inhalation begins and causes the bottom portion of the valve assembly to seal the fluid channel air inlet, the air inlet flap 40 is drawn open by the continuing negative pressure and allows ambient air into the chamber. This ambient air is drawn out through the chamber and the mouthpiece carrying the aerosol with it.

Figure 22:
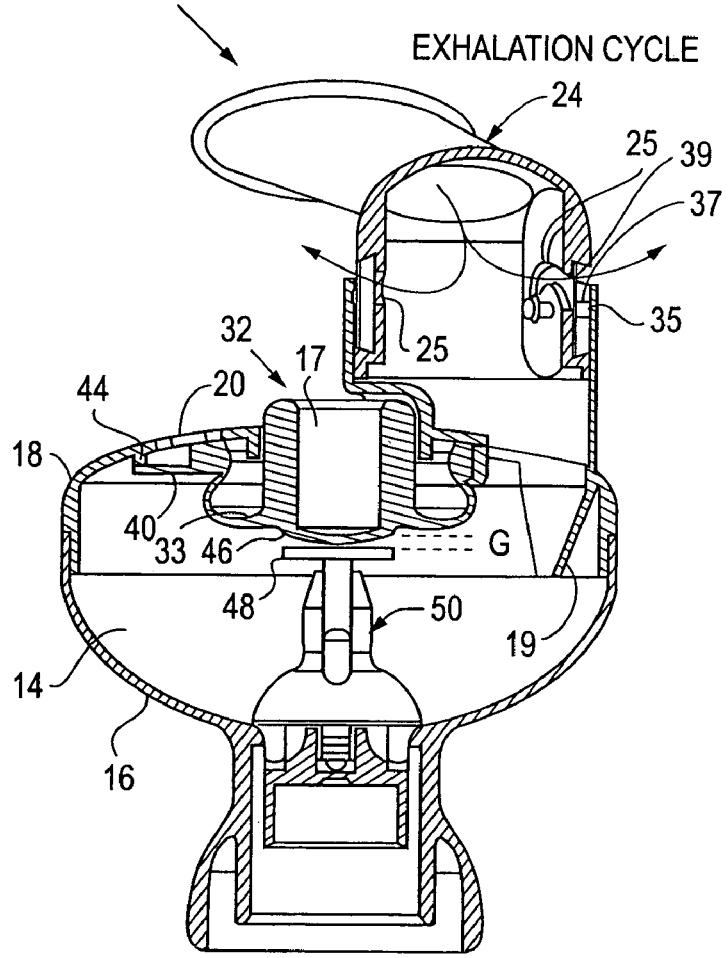
FIG. 22 is cross-sectional view of the nebulizer of FIG. 19 in a non-actuated position.
Figure 23:
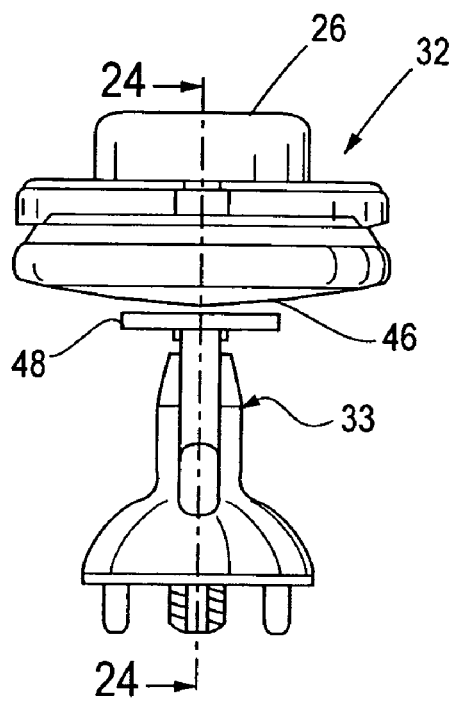
FIG. 23 is a side view of the valve assembly and nozzle assembly orientation with the nebulizer in a non-actuated state.
Figure 24:
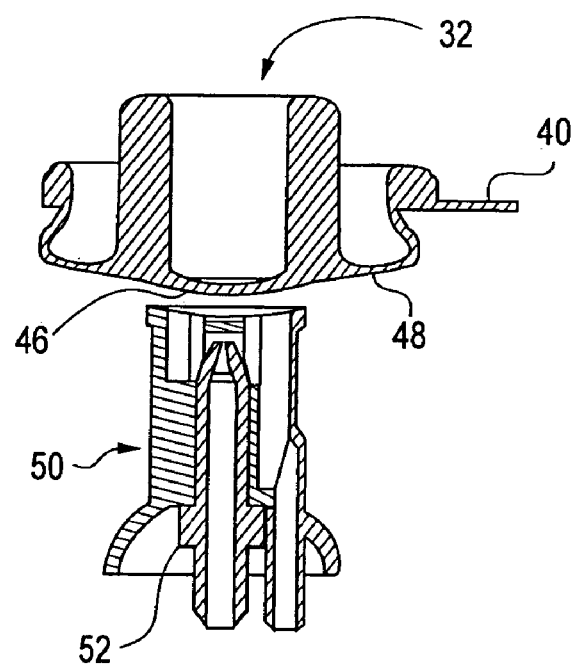
FIG. 24 is a cross-sectional view taken along lines 24-24 of FIG. 23.

The exhalation phase, shown in FIGS. 22-24, essentially reverses the process described above. When the patient ceases inhalation and begins exhalation, the inhalation valve flap 40 returns to its starting position and seals against the sealing ring 44 so that air/aerosol within the chamber 14 cannot escape through the air inlet 20 holes in the cover. The membrane of the valve assembly returns the bottom portion of the valve assembly to its starting position, spaced away from the valve seat and integral fluid channel air inlet openings. Once the fluid channel air inlet is open, ambient air can flow into the fluid channel air inlet and fluid will cease being drawn up through the fluid channel. Without the flow of fluid, nebulization ceases. Also, the increasing pressure in the chamber caused by patient exhalation will open the exhalation valves in the mouthpiece so that exhaled air is allowed to escape the nebulizer.

Figure 25:
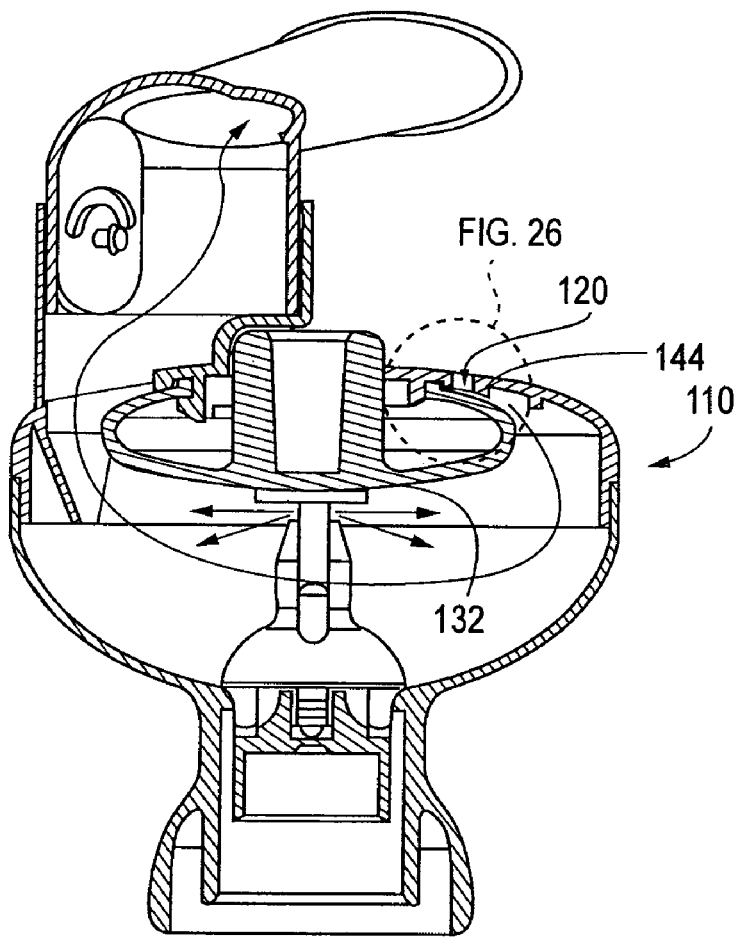
FIG. 25 is a cross-sectional view of an alternative embodiment of a nebulizer.
Figure 26:
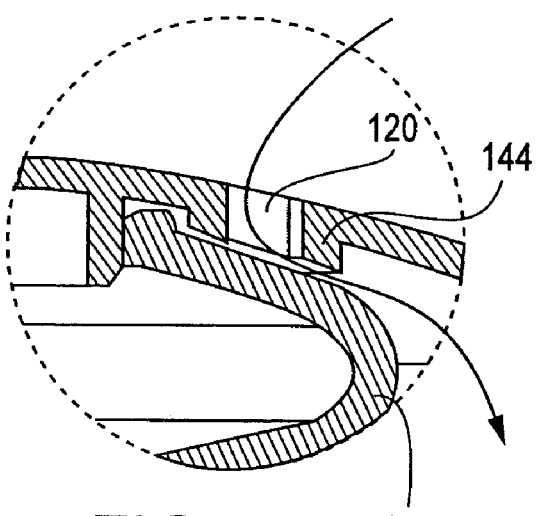
FIG. 26 is a sectional view depicting the air inlet of the nebulizer of FIG. 25 taken about line AA.

In one alternative embodiment of the nebulizer 110, illustrated in FIGS. 25-26, the body of the valve 132 is configured to function as both ambient air inlet valve and fluid channel air inlet valve, without a separate ambient air inlet flap. The combination valve 132 may be constructed with a curvature that cooperates with a sealing rim 144 of the air inlet 120 to keep the air inlet closed during exhalation and at rest, and flex in response to negative pressure in the chamber, or physical contact with the valve, to contact and seal against a fluid channel air inlet in the nozzle assembly to initiate nebulization. As inhalation continues and further reduces the pressure in the chamber, the valve 132 flexes and moves away from the sealing rim of the air inlet to allow ambient air into the chamber. Other variations of valve shapes and membranes are also contemplated.

Although a flexible flap and mushroom valve have been shown as one preferred ambient air inlet valve and fluid channel air inlet valve respectively, these valves may be any type of pressure release valve that will not move or open until the negative pressure within the nebulizer reaches a desired level, in this example, the fluid channel air inlet valve would close at 0.5-1.0 cm $H_2O$ and the ambient air inlet valve would open at 1.0-2.0 cm $H_2O$. Additionally, the diameter of the fluid channel air inlet is preferably selected such that the negative pressure generated within the fluid channel when the nebulizer is at rest is less than the negative pressure necessary to draw the liquid up through the fluid channel to the liquid orifice. The exact dimensions necessary for the fluid channel air inlet are dependent on the distance from the nozzle region to the top of the liquid in the vial. For example, if the vertical distance from the fluid orifice to the top of the liquid surface in the vial contained in the handle is 2 cm, then the negative pressure above the fluid in the fluid channel must be less than 2 cm $H_2O$ when the nebulizer is in its at rest phase.

In one preferred embodiment, the diameter of the fluid channel air inlet is 1.8 mm. In order to adjust the sensitivity of the fluid channel air inlet to a patient's breathing, the fluid channel air inlet valve may be constructed of a material or material thickness that is more responsive to changes in air pressure, the spacing between the fluid channel air inlet valve and valve seat may be adjusted, and the diameter of the fluid channel air inlet may be selected to be of a suitable size to change the sensitivity. The diameter, thickness, geometry, and durometer of the fluid channel air inlet valve are all factors which may be selected to adjust responsiveness.

Preferably, the diameter and position of the fluid channel air inlet valve is such that a patient or caregiver may also manually actuate the nebulizer by applying pressure to the valve through physical contact by hand or other object.

Figure 27:
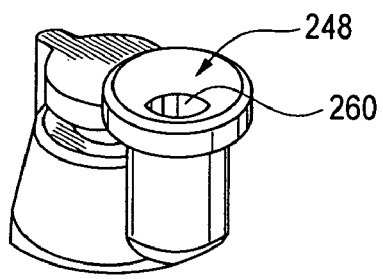
FIG. 27 is a first alternative embodiment of a valve seat for the fluid channel air inlet.
Figure 28:
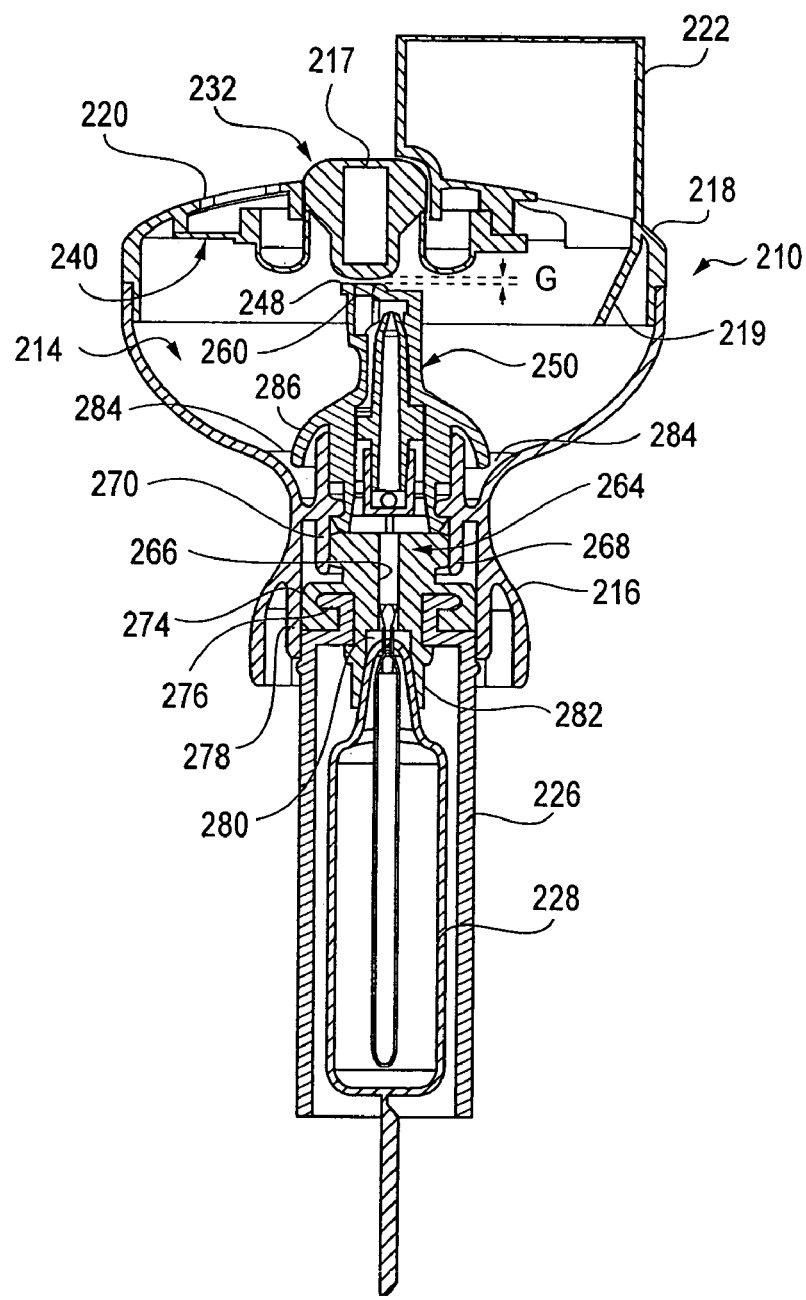
FIG. 28 is an alternative embodiment of the nebulizer of FIGS. 9-10 utilizing the valve seat of FIG. 27.

The fluid channel air inlet valve performance may also be modified by changing the number of fluid channel air inlets and the size and on topography of the valve seat. In other embodiments, a smaller valve seat 248 having a single air inlet 260 may be used as is shown in FIGS. 27-28. As with the valve seat 48 of the embodiment of FIGS. 1-2, this valve seat 248 is concave and circular so as to mate with a convex and circular-shaped bottom portion of the fluid channel air inlet valve and seal the fluid channel air inlet 260. The bottom portion 246 of the valve assembly 232 is sized to cooperate with the valve seat 248. Other than the cover 218, nozzle assembly 250 and valve 232 adjustments necessary to implement the single fluid channel air inlet, the remainder of the components of the nebulizer 210 shown in FIG. 28 are the same as those shown in FIGS. 9-10. Accordingly, the 200 series reference numbers in FIG. 28 correspond to the tens series reference numbers in FIG. 9 (e.g., reference 282 in FIG. 28=reference 82 in FIG. 9).

Figure 29:
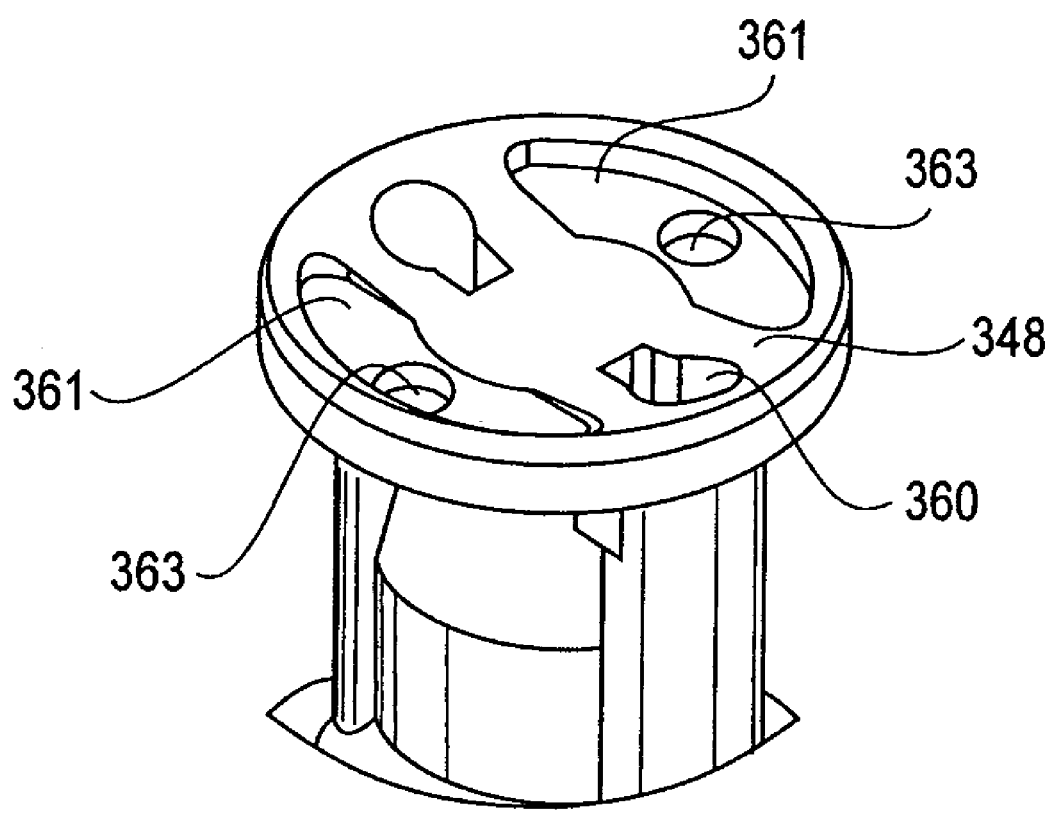
FIG. 29 is a second alternative embodiment of a valve seat for the fluid channel air inlet.

During nebulizer use, some amount of aerosol may impact or condense on the valve seat and valve, leaving a thin film of fluid. As shown in the embodiment of a valve seat 348 with two fluid channel air inlet openings 360, as illustrated in FIG. 29, the valve seat 348 may include a recessed regions 361 so as to reduce the region of contact between the valve and valve seat, and thus reduce the effect of potential surface tension that might result from the thin film of fluid and hinder separation of the valve from the valve seat 348 on exhalation. Also, pressure relief holes 363 may connect the recessed regions 361 to air in the chamber so that the recessed regions do not form partial vacuums that could impede responsiveness.

Figure 30:
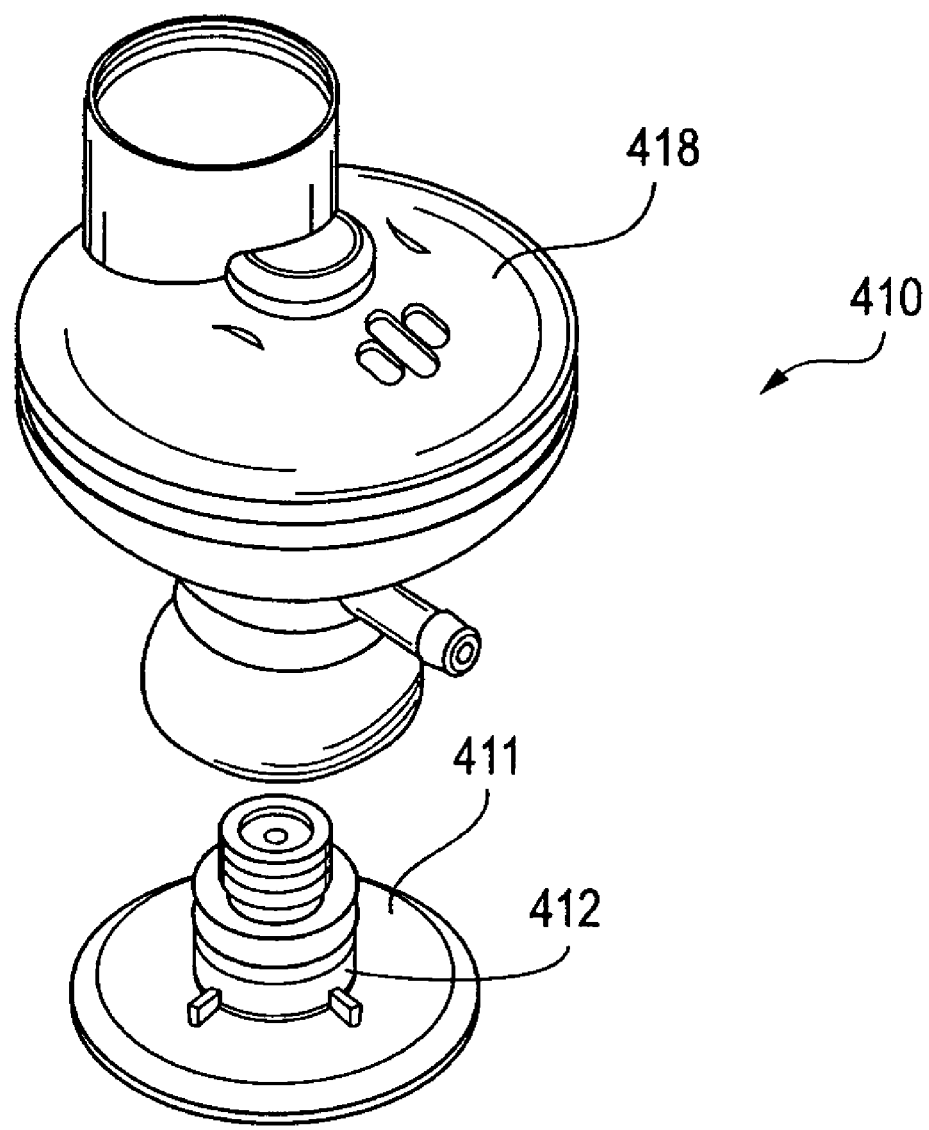
FIG. 30 is a partially exploded view of an alternative embodiment of the nebulizer of FIGS. 1-2 without a vial.

Another version of the nebulizer 410 is shown in FIG. 30. This nebulizer utilizes a base support 411, rather than a handle, to hold the fluid to be nebulized. The base support 411 may be suitable to receive a vial, or may be configured as a base plug that seals against the bottom of the nebulizer and forms a reservoir for holding the fluid to be nebulized. In embodiments where the base support is sized to hold a vial, the base support may be constructed in any of a number of configurations sized to accommodate the desired type or configuration of vial or other fluid container. In embodiments where the base support 411 itself defines a reservoir into which the fluid to be nebulized is provided, the reservoir and needle 66 are preferably sized to cooperate so that fluid may be withdrawn from the reservoir. In the non-vial embodiments, the fluid may be supplied to the reservoir by pouring the fluid into the nebulizer through the top, for example through the mouthpiece 24 or the outlet 22 in the cover 18. Alternatively, the base support 411 could be removed, filled with an appropriate amount of fluid, and reconnected to the rest of the nebulizer.

The base support 411 may permit the nebulizer 410 to stand on its own or to be held on a flat surface for greater stability during treatment. In one alternative embodiment, the base support 411 may include an adjustable height shaft 412. Concentric shaft components may form the shaft 412, where each component may have complementary threads or detents to adjust the height relative to the other components.

Figure 31:
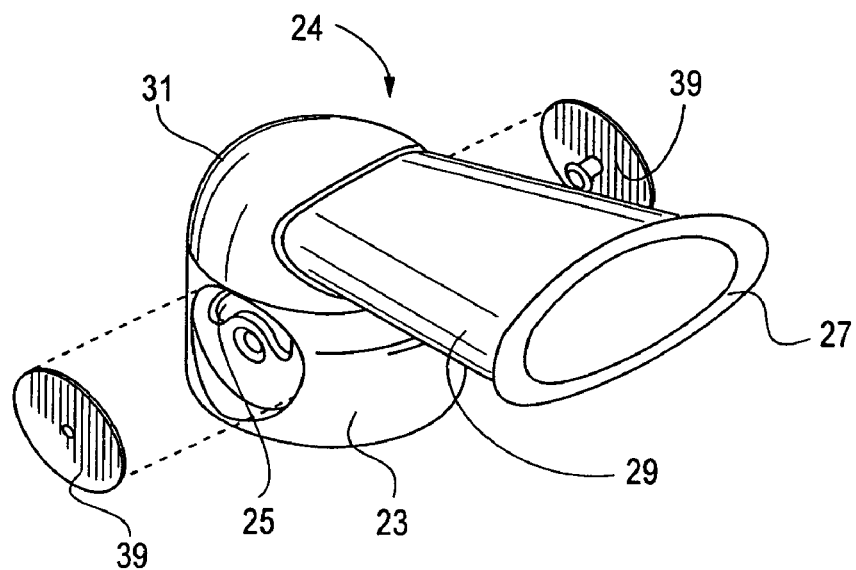
FIG. 31 is an exploded view of a mouthpiece suitable for use in the nebulizer of FIGS. 1-2.

Referring to FIGS. 22 and 31, a mouthpiece 24 suitable for use with the nebulizer 10 is shown in greater detail. The mouthpiece 24 includes a hollow vertical extension 23 sized to frictionally fit or snap-fit into the outlet 22. Two exhalation openings 25 are formed in the walls of the vertical extension and recessed to permit exhalation valve membranes to fit over the openings 25 and avoid contact with the inner wall of the air outlet 22. A mouthpiece opening 27 on the end of an angled shaft 29 is oval-shaped to roughly conform to the shape of a patient's mouth. The angled shaft 29 connects with the vertical extension at an elbow 31. In one embodiment, the angled shaft may connect with the elbow 31 at a point below the apex of the elbow so that a pocket of air is maintained inside the mouthpiece in the hollow top portion of the elbow. The pocket of air at the top of the elbow may assist in preventing aerosol impaction against the interior of the mouthpiece as aerosol is drawn into the angled shaft 29 from the vertical extension 23. In one alternative embodiment the elbow may include a hinge or joint permitting a patient to adjust the angle between the vertical extension 23 and angled shaft 29.

When assembled, the mouthpiece 24 is frictionally retained in the outlet 22 and is rotatable about the central axis of the outlet 22. A ridge 35 integrally formed on the outside of the vertical extension 23 cooperates with a complementary circumferential groove 37 on the inside wall of the air outlet 22 to both maintain the mouthpiece 24 in the outlet and guide the mouthpiece when rotated. As shown in FIGS. 19 and 22, the vertical shaft 23 of the mouthpiece is positioned in the air outlet such that the exhalation openings 25 are above the lip of the air outlet and the upper portion of the exhalation valve membranes 39 are free to flex outwardly from the recessed regions during exhalation to release exhaled air. Other suitable mouthpiece and exhalation valve configurations that may be adapted to fit to the air outlet 22 are illustrated in U.S. Pat. No. 6,044,841, the entire specification of which is incorporated herein by reference. Alternatively, a mask with an exhalation valve may be adapted to fit the air outlet 22. Suitable masks are disclosed in U.S. Pat. Nos. 5,988,160 and 5,645,049, the entire specifications of which are incorporated by reference herein. Also, a modified mouthpiece may be configured to connect to a mask that does not have exhalation valves, where the exhalation valves are located on the modified mouthpiece. Although a mouthpiece and a mask have been described, the nebulizer is suitable for use with, and may be constructed with, any of a number of known patient respiratory system interfaces, such as mouthpieces, masks, nasal prongs designed to interface with a patient's nasal passages, and other known interfaces.

Referring again to FIGS. 9-10, the nebulizer 10 is configured to avoid spillage of fluid from the chamber 14 or vial 28. Both of the openings of the ambient air inlet 20 and the aerosol actuator opening 30 are sealed by the valve assembly while the nebulizer is at rest. The connection between the cover 18 and base 16, which may be a friction fit connection, a threaded connection, or any of a number of detachable connections, forms a fluid seal as well. Also, the handle seal assembly 64 seals off the base 16 of the nebulizer and the opening of any attached vial. The remaining opening to the chamber, the air outlet 22, is protected by an anti-spill skirt 19 integrally formed on the inside of the cover 18. The anti-spill skirt 19 extends down from the lid along a portion of the circumference of the air outlet 22 and is centered at the portion of the air outlet opening closest to the outer edge of the cover. In this manner, fluid will be prevented from spilling out of the nebulizer through the air outlet by the dam created by the anti-spill skirt 19. In alternative embodiments, the anti-spill skirt may be angled as desired to increase the volume of fluid that can be held in the nebulizer should the nebulizer be inadvertently tipped over or laid on its side.

As shown in the figures, for example in FIGS. 10, 22 and 28, the gap between the diverter and the fluid and gas orifices is aligned in the same plane as the widest portion of the chamber 14. This alignment allows the aerosol generated in the nebulizer more room to form and reduces aerosol impact with the wall of the chamber. By providing the extra chamber space aligned with the nebulizing gap, particle size distribution in the aerosol drawn into a patient's lung may be improved. In one embodiment, the walls of the chamber curve or angle inwardly to the central axis of the nebulizer above and below the widest portion of the chamber. In alternative embodiments where the plane of aerosol generation is not the same as the plane of the nebulizing gap, the nebulizer chamber is preferably widest in the plane of aerosol generation. In other embodiments, the nebulizer may be configured to generate an aerosol in one direction rather than in a 360 degree manner as in the embodiment of nebulizer shown in FIGS. 10 and 22. In these embodiments, the chamber is preferably configured to be widest in the direction of the generated aerosol and on the same plane as the aerosol generation path. Thus, although the embodiment disclosed in FIGS. 9-10 and 22 possesses a chamber symmetric about a central axis and widest in the plane of the nebulizing gap, the nebulizer may have an asymmetric chamber aligned at its widest point with the plane of aerosol generated in embodiments having gas and fluid nozzles aligned to generate aerosol in a less than a 360 degree direction.

Also shown in FIGS. 10 and 22 is the relationship between the skirt 86 on the nozzle assembly 50 and the lower portion of the wall of the chamber 14. As described above with respect to this embodiment, aerosol is generated in a 360 degree direction. This aerosol, and the continuously flowing pressurized gas reflected off the diverter, can ricochet off of the walls of the chamber 14 in all directions. The ricocheting aerosol and gas can hit the chamber wall with enough force to hinder the tendency of condensed fluid on the walls to run down to the fluid return 88. By flaring out the base of the nozzle assembly and forming a protective skirt 86, the fluid can be shielded from the forces that hinder fluid return.

Another feature that can improve the performance and efficiency of the nebulizer is the suction assisted fluid return generated by the withdrawal of fluid from the vial 28 during nebulization. Because the vial and handle are connected to the base of the nebulizer with a fluid-tight seal, the act of withdrawing fluid from the vial results in a negative pressure in the vial. Referring to FIG. 13, this negative pressure is then transmitted through the gaps 98 between the needle 66 and the opening of the vial. In turn, the suction assist then travels to the fluid return opening 90 in the handle seal assembly so that fluid in the fluid return path 88 is biased back down into the vial. In other embodiments, the gap 84 between the chamber wall and the skirt 86 may be sized to enhance the suction assist at the edge of the skirt 86.

In the above-embodiments, a nebulizer capable of both breath actuation and manual actuation has been disclosed where a diverter, gas orifice, and liquid orifice are maintain in a fixed position with one another at all times. Nebulization is initiated by movement of a valve over the fluid channel air inlet that is in communication with the fluid channel linking the liquid orifice with the fluid in the vial. By using a flexible membrane as the biasing member of the fluid channel air inlet valve, a very fast and reliable response to both increased and decreased pressures within the chamber of the nebulizer may be realized. A variety of fluid channel configurations may be utilized with the fluid channel air inlet and fluid channel air inlet valve design discussed herein. As described above, the fluid channel may be a separate element from the pressurized gas nozzle or may be formed in cooperation with the pressurized gas nozzle. Similarly, the fluid channel may be contained in a single component of the nebulizer or formed from the mating of more than one assembly in the nebulizer. The valve seat for the fluid channel air inlet may have one or more openings in addition to recesses or channels to reduce surface tension or other effects that may reduce responsiveness. If a continuous nebulization is desired, rather than a breath actuated response, the nebulizer may be modified with a valve locking mechanism that continuously covers the fluid channel air inlets. The valve locking mechanism may be a latch or cover on the outside of the nebulizer sized to hold the button 17 extending out of the cover 18 in an actuated position.

In other embodiments, the fixed diverter may be replaced by a movable diverter, where the nebulizer may be fabricated with or without fluid channel air inlets. In these other embodiments, the bottom portion of the valve assembly may be configured to move, during inhalation, into a nebulizing position where the bottom portion is spaced at a distance from the gas nozzle so as to deflect pressurized gas over the fluid orifice and initiate nebulization. At rest and during exhalation, the valve assembly would move away from the nebulizing position so that the pressurized gas would no longer pass over the fluid orifice and thus cease nebulization. Although the valve assembly itself may be useful as the diverter, a separate diverter mechanism may be attached to the valve assembly.

As one example of a movable diverter embodiment, the nebulizer of FIGS. 6-8 may be modified to have a movable diverter by removing the diverter 62 positioned across from the pressurized gas orifice 55, and all or a central portion of the valve seat 48, so that the bottom portion 46 of the valve 32 can move into and out of a nebulizing position relative to the gas orifice and deflect the gas over the fluid orifice on inhalation. Additionally, a rigid or flexible extension may be connected with the valve 32 to receive and deflect the gas. Other examples of a movable diverter may be found in U.S. Pat. No. 5,823,179, issued Oct. 20, 1998, the entirety of which is hereby incorporated herein by reference.

It is intended that the foregoing detailed description be regarded as illustrative rather than limiting, and that it be understood that the following claims, including all equivalents, are intended to define the scope of this invention.

We claim:
1. A nebulizer system comprising:
a source of fluid for nebulization, wherein the source of fluid comprises a vial detachably connectable with the nebulizer; and
a nebulizer for nebulizing a fluid from the vial, the nebulizer comprising:
a housing having a chamber for holding an aerosol;
an air outlet communicating with the chamber for permitting the aerosol to be withdrawn from the chamber;
a pressurized gas inlet adjacent a fluid orifice, the pressurized gas inlet in communication with the chamber and the fluid orifice in communication with a fluid channel, wherein the pressurized gas inlet comprises a cone-shaped gas nozzle and a fluid nozzle comprises a coaxially positioned cone-shaped sleeve around the cone-shaped gas nozzle, and wherein a skirt portion extends radially outward from the cone-shaped fluid nozzle and extends substantially to an inner wall of the chamber;

a fluid reclamation opening defined by the inner wall of the chamber and an outer edge of the skirt portion;

a diverter positioned in the chamber adjacent to the pressurized gas inlet; and a fluid return channel in communication with the fluid reclamation opening and a fluid return opening in the vial, wherein a suction force generated by removal of fluid from the vial into the nebulizer during nebulization assists in recovering condensed fluid on a wall of the chamber; and a needle in communication with the fluid channel and removably positionable in an opening of the vial, the needle having a first cross-sectional shape along a first length such that a fluid return gap is defined between an outside of the needle and an inner diameter of an opening in the vial when the first length is positioned in the opening of the vial.

2. The system of claim 1, further comprising a mouthpiece having at least one one-way exhalation valve configured to allow air to escape the chamber upon exhalation.

3. The system of claim 2, wherein the mouthpiece is rotatably mounted in the air outlet.

4. The system of claim 3, wherein the at least one one-way valve comprises a flexible membrane positioned over an opening defined in a wall of the mouthpiece.

5. The system of claim 1, further comprising an anti-spill skirt positioned in the chamber adjacent the air outlet, wherein fluid from the nebulizer is prevented from escaping the nebulizer through the air outlet when the nebulizer is not actuated and is not in an upright position.

6. The system of claim 1, further comprising a fluid channel air inlet valve movably disposed across a fluid channel air inlet, wherein the fluid channel air inlet is in communication with the fluid channel and the fluid orifice.

7. The system of claim 6, wherein the fluid channel air inlet valve is positioned in the housing having a first side of the valve in contact with ambient air outside the chamber and a second side of the valve in contact with a body of air inside the chamber, whereby the valve is movable both by physical contact with the first side of the valve and in response to a pressure change in the chamber.

8. The system of claim 1, wherein the fluid return gap is in communication with the chamber via a fluid return path that is separate from the fluid channel.

9. The system of claim 1, further comprising an air inlet in communication with the chamber.

10. The system of claim 9, wherein the air inlet comprises an ambient air inlet.

11. The system of claim 9, wherein a one-way air inlet valve is disposed over the air inlet.

12. The system of claim 11, wherein the air inlet comprises an ambient air inlet.

* * * * *